United States Patent
McConnell et al.

(10) Patent No.: US 6,642,353 B1
(45) Date of Patent: Nov. 4, 2003

(54) PEPTIDE LIGANDS FOR THE ERYTHROPOIETIN RECEPTOR

(75) Inventors: Stephen J. McConnell, San Diego, CA (US); Dominic G. Spinella, La Costa, CA (US)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/646,691

(22) PCT Filed: Mar. 17, 1999

(86) PCT No.: PCT/US99/05842
§ 371 (c)(1),
(2), (4) Date: Sep. 20, 2000

(87) PCT Pub. No.: WO99/47151
PCT Pub. Date: Sep. 23, 1999

(51) Int. Cl.$^7$ ................................................ C07K 14/00
(52) U.S. Cl. ...................... 530/300; 530/326; 435/375; 930/90
(58) Field of Search ................................ 530/300, 326; 435/375; 430/90

(56) References Cited

U.S. PATENT DOCUMENTS

| | | | |
|---|---|---|---|
| 5,223,409 A | 6/1993 | Ladner et al. |
| 5,403,484 A | 4/1995 | Ladner et al. |
| 5,427,908 A | 6/1995 | Dower et al. |
| 5,663,069 A | 9/1997 | Ray et al. |
| 5,698,425 A | 12/1997 | Ligon et al. |
| 5,773,569 A | 6/1998 | Wrighton et al. |
| 5,830,851 A | 11/1998 | Wrighton et al. |

OTHER PUBLICATIONS

Akamalsu et al., "Construction of a Human Ig Combinatorial Library from Genomic V Segments and Synthetic CDR3 Fragments", J. Immunol. 151:4651–59 (1993).

Clackson et al., "In vitro selection from protein and peptide lLbraries", Trends Biotechnol. 12:173–184 (1994).

Dower et al., "Peptide Agonist of the Thrombopoietin Receptor as Potent as the Natural Cytokine", Science 276:1696–1699 (1997).

Karlsson et al., "Kinetic analysis of monoclonal antibody–antigen interactions with a new biosensor based analytical system", J. Immunol. Methods 145(1–2):229–240 (1991).

Kay et al, "An M13 phage library displaying random 38–amino–acid peptides as a source of novel sequences with affinity to selected targets", Gene 128:59–65 (1993).

Kitamura et al., "Identification and Analysis of Human Erythropoietin Receptors on a Factor–Dependent Cell line, TF–1", Blood 73:375–380 (1989).

McConnellet al., "Construction and screening of M13 phage libraries displaying long random peptides" Molecular Diversity 1:165–176 (1996).

Sawyer et al., "Rapid detection of antigen binding by antibody fragments expressed in the periplasm of *Escherichia colie*", Protein Engineering 4; 947–953 (1991).

Smith et al., "Libraries of Peptides and Proteins Displayed on Filamentous Phage", Methods in Enzymol. 217:228–257 (1993).

Wilson et al., "Functional Mimicry of a Protein Hormone by a Peptide Agonist: The EPO Receptor Complex at 2.8 A", Science (1996) p. 464–71, vol. 273, Issue 5274.

Wrighton et al., "Small Peptides as Potent Mimetics of the protein Hormone Erythropoietin", Science 273:458–463 (Jul. 1996).

*Primary Examiner*—Bennett Celsa
*Assistant Examiner*—Jon D. Epperson
(74) *Attorney, Agent, or Firm*—Daniel W. Collins

(57) ABSTRACT

Clones isolated from phage display libraries that bound to an erythropoietin (EPO) receptor probe are disclosed. Peptides encoded by sequences of those clones that bound to the EPO receptor are disclosed. A 12-mer amino acid consensus sequence, CXXGWVGXCXXW (where X represents one of many amino acids), common to the peptides that bound to the EPO receptor, but unrelated to the primary structure of EPO, is disclosed.

32 Claims, 9 Drawing Sheets

D F D V C R R G W V G H C K D W L S D E Y A S N P S Y P V P H S Y Y L N P P

5' -gas-tts-gas-gts-tgs-cgs-cgs-ggs-tgs-gts-ggs-cas-tgs-aas-gas-tgs-cts-ags-GAC-GAG-TAC - 3'

3' -CTG-CTC-ATG-cgs-tcs-tts-ggs-tcs-ats-ggs-cas-ggs-gts-tcs-ats-ats-gas-tts-ggs-ggs- 5'

| CLONE/ SEQ ID NO. | PEPTIDE SEQUENCE | REL.AFF. |
|---|---|---|
| ERBI/9 | DFDVCRRGWVGHCKDWLSDEYASNPSYPVPHSYYLNPP | 1.0 |
| B1/ 47 | DVHECRPGWVGHCKDWLSDEYASNRRSPEPHRNYPIPP | 8.6 |
| B2/ 48 | EAQGCRWGWVGNCKEWLGDEYAKNTGTPAEKGKSRNPP | 8.4 |
| B3/ 49 | GKEVCRRGWVGHCQEWPMDEYTRNPSHPVPHNSRHKTP | 1.0 |
| B4/ 50 | NIQGCIRGWVGQCKDWLRDEYAREHTNQETPNNLLNPP | 7.7 |
| B5/ 51 | GLGACRRGWVGHCNDWLNDEYAKKPGYAMPDGYPHNGT | 17.1 |
| B6/ 52 | SLEPCRGGWVGHCNEWQRDEYAINPKWPNAPIEDPNPL | 9.2 |
| B7/ 53 | DREGCRRGWVGQCKAWFNDEYAKPPKKPFRNSYSLGPA | 23.2 |
| B8/ 54 | DVEACGGGWVGHCNYWLRDEYASKPIKQVPPGNHNQPS | 22.7 |
| B9/ 55 | DFEDCQGGWVGHCNDWLGDEYARHPRYGATQTLSVNRH | 15.4 |
| B10/56 | DLEVCRGGWVGHCKDWIWDEYARNPRYPDPQRKEVKSP | 7.7 |
| B11/57 | NIQGCIRGWVGQCKDWLRDEYAREHTNQETPNNLLNPP | 6.4 |
| B12/58 | GLGACRRGWVGHCNDWLNDEYAKKPGYAMPDGYPHNGT | 4.1 |
| B13/59 | EGEVCLPGWVGHCKYWLMDEYANIPRNPTPRSNELKPP | 9.0 |
| B14/60 | EAQGCRWGWVGNCKEWLGDEYAKNTGTPAEKGKSRNPP | 3.4 |
| B15/61 | QVDTCTRGWVGHCNAWMGDEYAKTPGLPMPQSDYLKPR | 1.4 |
| B16/62 | DVEVCRGGWVGHCNAWLRDEYNRQPKKPVQQQVVYSTR | 0.8 |
| B17/63 | LLQMCSPGWVGHCNDWPRDEYANNPPNPVVDRQALTPP | 1.6 |
| B18/64 | YSDVCRRGWVGHCEDWLGDEYSSQPSYALPHSTSLNPR | 3.7 |
| B19/65 | DLEGCRLGWVGHCNVWGGDEYTKRTSHSVPPSHKSKLL | 1.0 |
| B20/66 | DLAGCRRGWVGHCSEWLRDEYTSNPRYPVAPSYRLQPP | 0.9 |
| B21/67 | AKVVCRNGWVGHCSAWLTDEYESNPNTRIPNTFDMKTP | 0.6 |
| N1/ 68 | RLEDGDEGRVWHSSDLLSDEYASTPSYPLTPNYYEYPP | <0.1 |
| N2/ 69 | GWAGCRSGGAGQCKEGAGDEYAENPSYPVPPRKHLNRL | <0.1 |
| N3/ 70 | DLNVGCPGYVGHCADWLGDEYPVHPNPEVPQTLNLKPH | <0.1 |
| N4/ 71 | ELDMLRGGGVGQSKESLRDEYDHKTSTPVPPNQKLPPP | <0.1 |
| N5/ 72 | NSDVTRRGWADHWREWNWDEYASTPTHPASHSSYLNPP | <0.1 |
| N6/ 73 | EWVYSRQSWGGQWKDGVRDEYTMTPGDPVANKYSLMTP | <0.1 |
| N7/ 74 | EFVVWPRGWVGHCKGCRVDEYSGDPSNLEAQTHDMNFQ | <0.1 |
| N8/ 75 | GLNICRPGWVGHCNDSLRDEYATNPRTPGPLSYNLQPT | <0.1 |
| N9/ 76 | SVDVCNQGGVGRCNDGLGDEYASKPSYQEAPRYNPNLR | <0.1 |
| N10/77 | DFEGSLREWDGDWPEWLRDEYAROPSYPNPHKANQKPP | <0.1 |
| N11/78 | ALDVGRWDGVGHCKGCLKDEYTTLDSKNNPQISQVSPT | <0.1 |
| N12/79 | DVEVGRRACVGYCQEFLRDEYTATPSYPDKHSNYLNPP | <0.1 |
| N13/80 | DIAVCRGGCVGLCEEGLRDEYACNVKKPVPHSYKLNTP | <0.1 |

FIG. 4

PEPTIDE LIGANDS FOR THE ERYTHROPOIETIN RECEPTOR

FIELD OF THE INVENTION

The present invention relates to the fields of pharmacology and drug discovery. More particularly, the invention relates to novel peptide compositions that can bind and activate the human erythropoietin receptor, and to methods of making small molecule agonists of the erythropoietin receptor using such peptide compositions as design templates.

BACKGROUND OF THE INVENTION

Drug discovery traditionally has relied upon high-throughput screening of large numbers of chemical compounds to identify novel drug leads. More recently, combinatorial libraries constructed by chemical or biological means have greatly expanded the number of compounds available for screening. Biological libraries, such as phage displayed peptide libraries, of random directed semi-random sequences represent particularly rich sources of molecular diversity and advantageously possess the ability to self-replicate. With a self-replicating system, the search for high affinity leads is not limited to members that happen to be present in the initial library. As discussed more fully below, desired characteristics of initial sequences can be greatly improved by employing successive rounds of mutagenesis, affinity selection, and amplification. These approaches recently have been used to discover small peptides capable of binding several cytokine receptors.

Erythropoietin (EPO) is a cytokine that stimulates the formation of red blood cells by inducing the growth and differentiation of progenitor cells. The recombinant version of human EPO is a valuable therapeutic agent useful for treating anemia that is associated with several pathological conditions, including chronic renal failure, malignancy or the effects of chemotherapy, HIV and rheumatoid arthritis. When used therapeutically, EPO must be administered either by intravenous or subcutaneous injection. The fact that EPO is a relatively large glycoprotein adversely impacts the cost of manufacture, the pharmacological properties of molecule, and the mode of delivery of this therapeutic agent.

The erythropoietin receptor (EPOR) belongs to the cytokine receptor superfamily whose members share common structural features including an extracellular ligand binding domain, a single transmembrane-spanning region, and. an intracellular cytoplasmic domain. The extracellular domain (ECD) is sufficient to mediate receptor-ligand binding. It is therefore possible through recombinant DNA techniques to synthesize DNA encoding the ECD as a fusion with secreted proteins to produce reagents useful for identifying receptor binding molecules, for example by screening a phage display library.

Phage display libraries expressing fusions of random or semi-random peptides and bacteriophage coat proteins represent convenient versions of combinatorial libraries that can be screened to identify receptor ligands. Upon infection and assembly of phage particles, the random polypeptides are outwardly disposed for interaction with antibodies or other receptor probes. Since the phage particles contain the nucleic acid that encodes the fusion protein, the genetic information which identifies the sequence of the fusion protein is physically linked to the fusion protein. Construction and screening of such phage expression libraries are well known and have been described previously, such as, for example, in Sawyer et al., *Protein Engineering* 4:947–953 (1991); Akamatsu et al., *J. Immunol.* 151:4651–59 (1993), Smith et al., *Methods in Enzymol.* 217:228–257 (1993); Clackson et al., *Trends Biotechnol.* 12:173–184 (1994), and U.S. Pat. No. 5,427,908 to Dower et al.

In one example of a screening procedure, a soluble form of the EPOR was used to probe a phage display library to identify candidate peptides having EPO-like properties. Wrighton et al., in *Science* 273:458 (1996) described the use of a fusion protein comprising the EPOR extracellular domain and human placental alkaline phosphatase in a library screening protocol. The library used for this purpose displayed cyclic 8-residue peptides as fusions with the pVIII coat protein of a filamentous phage. Peptides having higher affinity for the EPOR were subsequently isolated from mutagenesis libraries that displayed pIII protein fusions. This approach led to the identification of several peptides that stimulated erythropoiesis in mice. These agonists were disulfide-bonded cyclic peptides having the minimum consensus sequence YXCXXGPXTWXCXP (SEQ ID NO:1), where X is a position that can be occupied by any of several amino acids.

Despite this progress toward identifying EPOR ligands, there remains a need to identify ligands exhibiting superior receptor-binding properties as well as ligands that bind to the receptor using previously unknown contact sites.

SUMMARY OF THE INVENTION

According to one aspect of the invention, there is disclosed an isolated polypeptide capable of binding to a human erythropoietin receptor, having the formula:

wherein $X_n$ is an amino-terminal peptide of from 2 to 4 natural α-amino acids in length; $X_C$ is a carboxy-terminal dipeptide; and $X_1$, $X_2$, $X_3$, $X_4$ and $X_5$ are independently selected from the group consisting of natural a-amino acids.

In preferred embodiments of the isolated polypeptide, the amino-terminal $X_n$ is $X_{n1}$-$X_{n2}$-$X_{n3}$-$X_{n4}$, wherein $X_{n1}$ is selected from the group consisting of neutral and polar, neutral and hydrophobic, and acidic natural a-amino acids, or optionally $X_{n1}$ is absent; $X_{n2}$ is selected from the group consisting of neutral and polar, neutral and hydrophobic, and basic natural a-amino acids, or optionally $X_{n2}$ is absent if $X_{n1}$ is absent; $X_{n3}$ is selected from the group consisting of natural α-amino acids; and $X_{n4}$ is selected from the group consisting of neutral and polar, neutral and hydrophobic, and acidic natural α-amino acids. More preferably, $X_{n1}$ is E, G, N, S, D, Q, L, Y or A; $X_{n2}$ is F, V, A, K, R, G, S, I or L; $X_{n3}$ is H, Q, E, G, D, A, or V; and $X_{n4}$ is E, G, V, A, P, D, T or M. In other preferred embodiments, $X_{n1}$ is absent; $X_{n2}$ is F, V, A, K, R, G, S, I or L; $X_{n3}$ is H, Q, E, G, D, A, or V; and $X_{n4}$ is E, G, V, A, P, D, T or M. In one embodiment $X_{n1}$ is an acidic amino acid. In another embodiment, $X_{n2}$ is a branched-chain amino acid or K. In yet another embodiment, $X_{n3}$ is an acidic amino acid or V. In one embodiment, $X_{n4}$ is V or G. In preferred embodiments, $X_1$ is a neutral and hydrophobic, neutral and polar, or basic amino acid; more preferably $X_1$ is R, I, G, Q, L, T or S; and most preferably, is R or I. In preferred embodiments, $X_2$ is a neutral and hydrophobic, neutral and polar, or basic amino acid; more preferably, $X_2$ is R, P, W, G, L or N; and most preferably is R. In preferred embodiments, $X_3$ is a neutral and polar, or basic amino acid; and more preferably $X_3$ is H, Q or N. In preferred embodiments, $X_4$ is a neutral and polar, basic, or acidic amino acid; more preferably $X_4$ is Q, N, S, K or E; and most preferably is K or N. In preferred embodiments, $X_5$ is a neutral and polar, neutral and hydrophobic, or acidic amino acid; more preferably is V, A, Y, D or E; and most preferably is D or E. In preferred embodiments, the carboxy-terminal $X_c$ is $X_{c1}$–$X_{c2}$ and wherein $X_{c1}$ is a neutral and polar, or neutral and hydrophobic amino acid, and $X_{c2}$ is a neutral and polar, neutral and hydrophobic, or basic amino acid. In preferred embodiments, $X_{c1}$ is L, I, P, F, M, Q or G; and more preferably is L or Q. In preferred embodiments, $X_{c2}$ is M, W, T, S, G, N or R; and, more preferably, $X_{c2}$ is G or R.

Other aspects of the invention are isolated polypeptides having the amino acid sequences of SEQ ID NO:81 and SEQ ID NO:82.

According to another aspect of the invention, there is disclosed a method of activating a human erythropoietin receptor, comprising the steps of contacting a cell having an erythropoietin receptor on it surface with a peptide mimetic of erythropoietin, wherein the peptide mimetic is a compound having the general formula $$X_n\text{-}C\text{-}X_1\text{-}X_2\text{-}G\text{-}W\text{-}V\text{-}G\text{-}X_3\text{-}C\text{-}X_4\text{-}X_5\text{-}W\text{-}X_C$$

wherein $X_n$ is an amino-terminal peptide of from 2 to 4 natural α-amino acids in length; $X_C$ is a carboxy-terminal dipeptide; and $X_1$, $X_2$, $X_3$, $X_4$ and $X_5$ are independently selected from the group consisting of natural α-amino acids; and allowing the peptide mimetic to bind to the erythropoietin receptor, thereby initiating activation of the erythropoietin receptor.

Another aspect of the invention that is disclosed is a method of inhibiting binding of erythropoietin to an erythropoietin receptor, comprising the steps of providing a peptide mimetic having the general formula $$X_n\text{-}C\text{-}X_1\text{-}X_2\text{-}G\text{-}W\text{-}V\text{-}G\text{-}X_3\text{-}C\text{-}X_4\text{-}X_5\text{-}W\text{-}X_C$$

wherein $X_n$ is an amino-terminal peptide of from 2 to 4 natural α-amino acids in length; $X_C$ is a carboxy-terminal dipeptide; and $X_1$, $X_2$, $X_3$, $X_4$ and $X_5$ are independently selected from the group consisting of natural α-amino acids, in sufficient quantity to compete with erythropoietin for binding to an erythropoietin receptor; and allowing the peptide mimetic to interact with the erythropoietin receptor, thereby inhibiting binding of erythropoietin to the erythropoietin receptor. In a preferred embodiment, the erythropoietin receptor is derived from a human.

Another aspect of the invention is a method of discovering drugs that mimic erythropoietin, comprising the steps of constructing a phage display library in which a fusion protein comprising a peptide consisting of a random sequence of amino acids and a phage protein; screening the phage display library for at least one clone that binds to a human erythropoietin receptor probe; isolating the clone that bind to a human erythropoietin receptor probe; determining a nucleic acid sequence from the clone that codes for the peptide contained within the fusion protein; constructing an evolved phage display library by mutagenesis in vitro of the nucleic acid sequence that codes for the peptide contained within the fusion protein; screening the evolved phage display library for clones that bind to a human erythropoietin receptor probe; isolating the clones from the evolved phage display library; determining nucleic acid sequences from the clones, wherein each nucleic acid codes for a peptide contained within the clone's fusion protein; comparing the nucleic acid sequences to identify a consensus amino acid sequence; and synthesizing a compound that mimics the consensus amino acid sequence. In a preferred embodiment, the synthesizing step includes synthesizing a compound that is an organic compound, preferably a peptide. More preferably, the synthesized peptide is a cyclic peptide.

BRIEF DESCRIPTION OF THE DRAWINGS

FIGS. 3A and 3B show the approach that was used to create an ERB1 evolved library. FIG. 3A shows the amino acid sequence (SEQ ID: 9) of the peptide that was fused to the pIII protein in the ERB1 clone on the first line and the sequences of a collection of redundant oligonucleotides that were used to create the evolved library of the ERB1 clone on the second and third lines. The oligonucleotides have been aligned to show the codons corresponding to the amino acid in the ERB1 peptide and to show annealing of the oligonucleotides using 9 complementary bases at the 3' ends of the sequences. FIG. 3B shows the nucleotide compositions that were used to synthesize the redundant oligonucleotides, for each of the bases represented as "g", "a", "t", "c" and "s" in the redundant oligonucleotides. Depicted are the amino acid sequence of the peptide that was fused to the pIII protein in the ERB1 clone and the scheme that was used to create a collection of oligonucleotides that encoded variants of the ERB1 peptide sequence.

FIG. 4 shows the amino acid sequences of phage clones derived from the ERB1 evolved library and relative affinities of the clones for Ig-EPOR. Clones B1 to B-21 were isolated by binding to Ig-EPOR, and phage clones N1 to N13 were derived from the evolved library but did not bind to Ig-EPOR during the selection process. The relative affinities are numerical summaries of the data presented in FIGS. 5A to 5D.

FIG. 5A shows results for clones B1 to B5 and ERB1; FIG. 5B shows results for clones B6 to B10 and ERB1; FIG. 5C shows results for clones B11 to B15 and ERB1; and FIG. 5D shows results for clones B16 to B21 and ERB1.

FIG. 8A shows a dose response curve for proliferation of TF-1 cells (O.D. at 450 nm) at different concentrations (Units) of recombinant EPO; and FIG. 8B shows a dose response curve for proliferation of TF-1 cells (O.D. at 450 nm) at different concentrations (µM) of the synthetic peptides ERB1-7 ( ) and ERB1-8 ( ), compared to addition of an irrelevant peptide that binds to IL-6 receptor (x).

DETAILED DESCRIPTION OF THE PREFERRED EMBODIMENT

Figure 1:
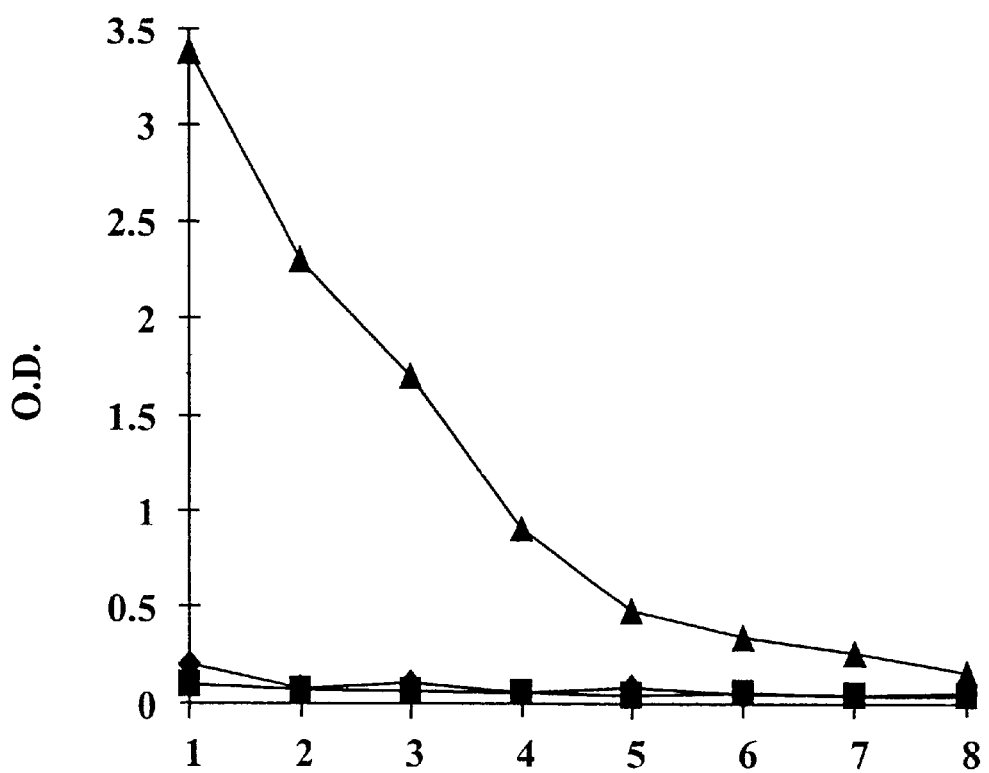
FIG. 1 is a line graph showing results from an EPOR-specific phage ELISA which confirmed that the ERB1 phage clone specifically binds the chimeric Ig-EPOR probe. The graph shows binding to Ig-EPOR as measured by an ELISA (O.D.) at different phage dilutions for a phage clone (ERB1,) isolated using the Ig-EPOR probe; for a phage clone (HPKF,) that binds specifically to an anti-IL-8 antibody, and for a phage clone (IL6-B26,) that binds specifically to the human IL-6 receptor.

Herein we disclose both novel peptides that can bind and activate the human EPOR and methods of making small molecule analogs of EPO using peptide ligands as design templates. Unexpectedly, the primary amino acid sequences of these peptide ligands are unrelated to the primary amino acid sequence of the authentic EPO protein. Moreover, the peptides disclosed herein also are unrelated to previously isolated EPOR binding peptides from phage display libraries. The novel peptides identified herein serve not only as candidate therapeutic agents, but also as models for designing small molecules having EPO agonist or antagonist activities. Clearly, peptides or other small molecules that mimic the biological properties of EPO would represent valuable additions to the pharmacopeia.

A collection of cyclic peptides that bind the EPOR and mimic the pharmacological activity of erythropoietin were identified. One EPOR-binding clone was initially isolated from an M13 phage library displaying 38 random amino acids fused to the N-terminus of the pIII capsid protein. Using the sequence coding for the EPOR-binding peptide of this initial isolate, an evolved library containing a variety of amino acid substitutions over the entire length of the peptide was made and screened using biopanning to isolate additional EPOR-binding clones. The sequences coding for the binding peptides, and non-binding controls, were determined. Neither the initial isolate nor any of the EPOR-binding clones isolated from the evolved library shared significant sequence similarity with the primary amino acid sequence of EPO. The sequences of the EPOR-binding clones included a consensus sequence that was absent from non-binding clones. This consensus sequence (SEQ ID NO:12) codes for a 12-mer peptide, although additional amino acid residues also contribute to efficiency of binding to EPOR.

Based on the consensus sequence, truncated peptides of 18 amino acids in length were synthesized that retained the activity of the longer 38-mer binding peptide. Two exemplary synthetic peptides, having amino acid sequences based on the consensus 12-mer sequence, inhibited binding of authentic EPO to a chimeric Ig-EPOR in an in vitro assay. Moreover, these derivative peptides also stimulated proliferation of an EPO-responsive cell line in culture. Truncating one of the 18-mer synthetic peptides by one or more N-terminal residues decreased the peptide activity in receptor-binding and biological assays. Thus, although longer peptides containing at least an 18-mer amino acid sequence showed high affinity binding to EPOR, smaller peptides (e.g., having three amino acids located N-terminal to the consensus sequence) retained the ability to activate EPOR Briefly, the EPOR ligands disclosed herein were identified by a multi-step procedure that involved: (1) creating a chimeric receptor probe that binds EPO; (2) creating a phage display library expressing a large number of target random peptides; (3) screening the library with the chimeric receptor probe to identify one or more lead peptides having receptor-binding activity; and (4) creating and testing derivatives of the lead peptides to identify structural features common to variant molecules that bind and/or activate the EPO receptor. Below are described certain general features of the methods that were used to obtain the novel EPOR agonists.

A Chimeric Receptor Probe Having EPO Binding Activity

Methods for identifying receptor ligands have relied on the binding of anti-ligand antibodies or subfragments of native receptor ligands which may inherently bias the outcome of the screening assay. For example, because linear peptides of only 6–10 amino acids in length can be accommodated into the combining site of an antibody, it is difficult to identify peptides that represented tertiary structures that might be critical structural features of receptor-binding ligands. Similarly, subfragments of known ligands may not represent critical higher-order structures that have or represent common structural features of the cognate ligand. For example, tertiary structure of receptor-binding ligands might not be completely contained in contiguous amino acids of and antibody or other ligand.

To avoid unnecessary limitations on the structures of combinatorial molecules that could be identified in a binding assay, we created a probe that contained the extracellular domain the native receptor. For convenience in the screening assay, we also employed a probe that not only could bind the ligand, but also that could be identified by a secondary probe. We created a chimeric protein that incorporated a ligand binding domain of the EPO receptor ("EPOR") and the hinge region, CH2 and CH3 domains of the murine IgG1 antibody. As indicated below, this chimeric receptor ("Ig-EPOR") bound native ligand and also was recognized by an anti-murine IgG. This arrangement allowed the probe to bind novel ligands that exhibited critical minimal structural features of the native ligand that were required for receptor interaction and also be detected using a secondary antibody.

Advantageously, the use of a probe that included the ligand binding domain of the native receptor allowed binding of structures as large as the native ligand or as small as the minimal critical structure needed for receptor binding.

Construction and Screening of a Phage Display Library

We have employed high complexity phage display libraries as the source of molecular diversity for drug discovery. Whereas traditional libraries of organic compounds conventionally are screened one compound at a time to identify candidate drug molecules, phage display libraries offer a rich source of molecular diversity which can be rapidly screened using high throughput screening assays.

The libraries employed in the screening procedures disclosed below displayed fusions with the pIII minor coat protein of phage M13. While the N-terminal domain of the pIII molecule binds the bacterial F pilus and is required for infection, the C-terminal domain anchors the protein in the phage capsid. Advantageously, fusions of a large range of sizes can be tolerated in the constructions that involve the pIII protein, thereby enhancing the molecular diversity of the library. Relatively long random amino acid sequences (e.g., about 30 to about 50 residues) can be fused to the pIII protein to display relatively large peptides comprising random sequences for screening.

Libraries of long random peptides offer a "sliding window" of adjacent amino acid residues, and also have the potential of providing tertiary structures that represent discontinuous epitopes in complex proteins. This added level of complexity may be important when screening for molecules capable of interacting with complex targets such as cell surface receptors. Moreover, libraries of long random peptides make possible the formation of multiple contact sites that are capable of binding complex targets.

Production and Testing of Derivatives of Lead Peptides

We identified and isolated an initial isolate from one of the phage display libraries as a lead peptide and then constructed molecular variants of that lead peptide and screened for clones that exhibited similar or enhanced biological activities. That is, we created a phage display library in which nearly all of the codon positions in the 38-mer lead peptide were randomized at a predicted frequency of 50% to generate a library of variant molecules. By screening the library of variants, we identified a large number of additional peptides that also bound the EPO receptor probe. Alignment of peptide sequences deduced from the DNA sequences of the variants allowed us to identify a consensus sequence of amino acids for molecules that possessed the desired functional characteristics. Herein, this process of creating libraries of variant peptides based on the nucleic acid sequence coding for a lead peptide is referred to as "molecular evolution." Using this process, we identified mutant clones having increased ability to interact with a receptor of interest (i.e., clones with increased binding affinity for the EPOR relative to that of the lead clone).

The molecular evolution process allowed us to screen greater than 100 million protein variants to identify additional functional peptides. Alignment of the amino acid sequences of these additional peptides and identification of a consensus sequence served as a basis for identifying optimized receptor binding peptides. Preferably, these optimized peptides are smaller than the peptide present in the lead isolate, and more preferably, the optimized peptides are smaller than the variants identified by using molecular evolution.

Definitions

By "chimeric protein" is meant a non-naturally occurring protein or polypeptide comprising some or all of the amino acid sequences from at least two different proteins or polypeptides, or of one protein or polypeptide and a non-naturally occurring polypeptide chain. As used herein, a chimeric protein is designed, constructed by genetic engineering, synthesized, or otherwise selected intentionally, and contains at least two domains (i.e., at least a first domain and a second domain, each having some structural and/or functional characteristic that is not present in the other domain).

By "directly or indirectly labeled" is meant that a molecule may contain a label moiety which emits a signal which is capable of being detected directly (e.g., radioisotope, dye, or fluorescent or chemiluminescent moiety), or may contain a moiety which, through some additional reaction (i.e., indirectly), is capable of being detected (e.g., an attached enzyme, ligand such as biotin, enzyme substrate, epitope, or nucleotide sequence).

By "secondary molecule" is meant a molecule which is able to bind to at least a portion of the second domain of a chimeric protein, thereby allowing detection or purification of the chimeric protein.

By "hinge region" or "immunoglobulin heavy chain hinge region" is meant one of a family of proline-containing and cysteine-containing amino acid sequence regions which occur between the $C_{H2}$ and $C_{H1}$ regions of many mammalian immunoglobulin heavy chains, or analogs of these amino acid sequences based thereon, in which the regions to the amino- and carboxyl-terminal sides of the hinge are spatially separated by a turn or kink in the polypeptide chain, to facilitate separate and simultaneous specific binding to other molecules.

By "ligand" is meant a molecule or a multimeric molecular complex which can specifically bind to another given molecule or molecular complex (i.e., its target). Often, though not necessarily, a ligand is soluble while its target is immobilized, such as by an anchor domain imbedded into a cell membrane.

By "receptor" is meant at least a portion of a molecule or a multimeric molecular complex which, in its native environment, has an anchor domain embedded into a cell membrane and is able to bind a given molecule or molecular complex. Often a receptor is capable of transducing an intracellular signal in response to ligand binding. Many receptors have particularly high affinity for a ligand when either or both the receptor or ligand are in a homomultimeric or heteromultimeric form (e.g., a dimer).

By "solid support" is meant an insoluble matrix either biological in nature, such as, without limitation, a cell or bacteriophage particle, or synthetic, such as, without limitation, an acrylamide derivative, cellulose, nylon, silica, and magnetic particles, to which soluble molecules may be linked or joined.

By "modified" is meant non-naturally occurring or altered in a way that deviates from naturally-occurring compounds.

By "molecular evolution" is meant a process of creating a library of variant peptides by randomization, at a controlled rate, of a nucleic acid sequence coding for a lead peptide having desired functional characteristics.

By "molecule" is meant a molecular-sized inorganic or organic compound, such as, for example, a peptide, protein, nucleic acid, fat or fatty acid, which may be naturally ocurring or synthetically produced.

By "multimeric molecular complex" is meant a complex comprising at least two molecular components, where the individual components may be, for example, a peptide, protein, nucleic acid, fat or fatty acid, where the complex is held together by covalent bonds, non-covalent bonds or other known chemical interactions.

Amino acids, described by either their three letter (or one letter) abbreviations, are classified according to the nature of their side-groups (as described in Genes V, B. Lewin (Oxford University Press, Inc., New York, N.Y., 1994). These groups are: "neutral and hydrophobic" which includes Ala (A), Val (V), Leu (L), Ile (I), Pro (P), Trp (W), Phe (F) and Met (M); "neutral and polar" which includes Gly (G), Ser (S), Thr (T), Tyr (Y), Cys (C), Glu (Q) and Asn (N); "basic" which includes Lys (K), Arg (R) and His (H); and "acidic" which includes Asp (D) and Glu (E). "Branched-chain amino acids" refers to I, L and V.

Unless defined otherwise, all scientific and technical terms used herein have the same meaning as commonly understood by those skilled in the relevant art. General definitions of many of the terms used herein are provided in *Dictionary of Microbiology and Molecular Biology*, 2nd ed. (Singleton et al., 1994, John Wiley & Sons, New York, N.Y.), and *The Harper Collins Dictionary of Biology* (Hale & Marham, 1991, Harper Perennial, New York, N.Y.), and in protocol manuals listed below.

Identifying EPOR Binding Peptides

The procedures described herein were used to identify EPOR binding peptides that could be used as receptor agonists for treating humans and animals, and as structural templates for the design of small molecule EPO mimetics that have similar applicability. Short peptides or small molecule EPO mimetics that stimulate erythropoiesis would have clear advantages over recombinant EPO with respect to convenience of delivery, pharmacokinetics, and production costs.

We identified peptide mimetics of EPO by screening high complexity (about $10^8$ diversity) phage display libraries to identify EPOR binding peptides. The libraries displayed random peptide sequences as pIII fusion proteins expressed on the surface of M13 phage particles. Phage having the desired binding activity were affinity purified from the vast excess of non-binding phage, and the DNA of the purified phage was isolated, amplified and sequenced to determine the amino acid sequence of the displayed peptide.

In a typical phage display library, random peptides are displayed on the surface of bacteriophage M13 as N-terminal fusions expressed on major (e.g., pVIII) or minor (e.g., pIII) coat proteins. Individual bacteriophage particles displaying sequences having desirable binding characteristics can be affinity purified and cloned using standard laboratory techniques. Most phage libraries are constructed to display random sequences of only 6 to 8 amino acids in length as pIII or pVIII fusion proteins. Longer random peptides displayed on phage libraries, however, have potential advantages including increased complexity due to a "sliding window" effect (e.g., a 38-mer peptide contains 32 overlapping hexamers) and ability to assume tertiary structures independent of the native phage protein to which the peptides are fused.

As disclosed herein, we screened phage display libraries displaying relatively long peptides using an IgG-EPO receptor fusion protein to identify and isolate initial and evolved EPO peptide mimetics. Although the process employed below is generally applicable to the discovery of peptides that bind virtually any receptor, particularly any type I cytokine or growth factor receptor, the structure of the peptides discovered by this route cannot be predicted in advance of actually isolating and sequencing the clones which encode the peptides.

By determining the DNA and predicted amino acid sequences of peptides in clones isolated from an evolved library that bound to the EPOR probe, and sequences from clones that did not bind to this probe, a 12-mer consensus sequence of amino acids was identified as present in all of the clones that bound to the EPOR probe. This consensus sequence is CXXGWVGXCXXW, where X's represent a variety of amino acids.

In addition to the 12-mer consensus sequence, examination of the amino acid sequences of the 38-mer peptides of the binding clones (see FIG. 4 herein) showed that the first residue was an acidic, or neutral and polar, or neutral and hydrophobic amino acid, preferably D, E, G, N, S, Q, L, Y or A, and more preferably D. The second residue was a basic, or neutral and polar, or neutral and hydrophobic amino acid, preferably L, V, I, K, A, F, R ,G or S, and more preferably a branched-chain amino acid, most preferably L. The third residue was any of the four general types of amino acids characterized by the nature of their side chains, and preferably was E, D, Q, G, H, V or A, more preferably E or Q. The fourth residue was an acidic, or neutral and polar, or neutral and hydrophobic amino acid, preferably G, T, V, A, P, M, D, or E, and more preferably V or G. The fifth residue was C of the consensus sequence. The sixth residue was a basic, or neutral and polar, or neutral and hydrophobic amino acid, preferably R, L, I, ,G, Q, T or S, and more preferably R. The seventh residue was a basic, or neutral and polar, or neutral and hydrophobic amino acid, preferably R, G, N, P, W, or L, and more preferably R. Residues 8 to 11 are the GWVG sequence of the conserved 12-mer. Residue 12 was H, Q or N, preferably H, and the thirteen residue was the conserved C of the 12-mer. The fourteenth residue was acidic, or basic or neutral and polar, preferably E, K, N, Q or S, more preferably N or K. The fifteenth residue was an acidic, or neutral and polar, or neutral and hydrophobic amino acid, preferably D, E, Y, V or A, and more preferably D or E, most preferably D. The sixteen residue was W of the consensus 1 2-mer and the seventeenth residue was a neutral and polar, or neutral and hydrophobic amino acid, preferably Q, G, L, I, P, F or M, and more preferably L. The eighteenth residue was a basic, or neutral and polar, or neutral and hydrophobic amino acid, preferably R, G, N, T, S, M or W, and more preferably R or G. Residues 19 to 21 were the invariant DEY sequence conserved in all of the peptides due to the mutagenesis scheme used (see Example 7 below).

Residues 22 to 38 of the peptides shown in FIG. 4 also included subsets of the 20 naturally occurring α-amino acids. Notably, residue 22 was A, T, N, S or E, preferably A; residue 23 was K, R, S, N or I, preferably K or R; residue 24 was P, I, N, T, Q, K, H, R or E, preferably N; residue 25 was P, T, R or H, preferably P; residue 26 was I, P, S, G, T, N, R or K, preferably R or G; residue 27 was L, S, N, T, Y, H or K, preferably Y; residue 28 was P, A, Q, G or S, preferably P; residue 29 was a branched chain amino acid, A, M, F, N, T, E or D, preferably V; residue 30 was P, A, V, T, Q, R or E, preferably P; residue 31 was P, N, Q, H, K, R or D, preferably P; residue 32 was I, G, S, N, T, Q or R, preferably G or S; residue 33 was L, V, f, T, Y, N, S, Q, K, H, E or D, with N, Y or K appearing most frequently. Residue 34 was L, V, P, A, Y, S, K, R, H, D or E, preferably S; residue 35 was L, V, P, M, Y, N, S, R, or H, preferably one of the branched-chain amino acids, more preferably L. Residue 36 was 1, N, G, Q, S, T or K, preferably a neutral and polar amino acid, and more preferably N. Residue 37 was P, L, T, G, S or R, and residue 38 was P, L, A, T, S, H or R. Both residues 37 and 38 were preferably P. These amino acid residues represent the sequences of the population of 22 EPOR binding clones whose amino acid sequences are shown in FIG. 4, which are representative of binding peptides. Therefore, although certain trends in EPOR binding peptides may be discerned by examination of these sequences, particularly for preferred amino acids for some residues, they are not exclusive and EPOR binding peptides that retain the conserved 12-mer sequence with flanking sequences not shown by any of the sequences shown for binding clones in FIG. 4 are within the scope of this invention.

Many of the amino acids that appear preferably at a particular residue position in these evolved peptides were the same as the amino acid present at that position in the starting peptide (e.g., R at residue 5, and P at residue 25), which may reflect the mutagenesis scheme described in Example 7 (which synthesized nucleic acid sequences having 73% of the parental nucleotide and 9% of the other three nucleotides) and the redundancy of the genetic code. For some residues, however, there was considerable variation in the amino acids that appeared at that position (e.g., residue 33) and some residues in the binding clones appeared to selectively change to one or more amino acids that were not generally seen at that position in the non-binding clones. For example, residue 23 in the binding clones was preferably the basic amino acids K or R, representing a change from the neutral parental S residue, whereas K and R were not highly represented at residue 23 in the non-binding clones. Similarly, a higher percentage of the non-binding clones retained the parental H at residue 31 than the binding clones. Thus, in addition to the conserved 12-mer sequence, additional amino acids present in the evolved binding clones, or preferably not present compared to non-binding clones, probably contribute to the EPOR binding characteristic of the clone.

Although other materials and methods similar or equivalent to those described herein can be used in the practice or testing of the present invention, the preferred methods and materials are described in the examples that follow. Standard methods that can be used by those skilled in the art to perform the genetic engineering and other procedures described herein are found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987) and other well known references. Well known immunoassay methods including solid-phase immunoassays suitable for rapidly screening large numbers of peptides and other compounds are also known to those skilled in the art (see Harlow & Lane, *Antibodies, A Laboratory Manual*, 1988, Cold Spring Harbor Laboratory, Cold Spring Harbor, N.Y., particularly Chapt. 14, pp. 553–612).

The invention can be better understood by way of the following examples which are representative of the preferred embodiments, but which are not to be construed as limiting the scope of the invention.

Example 1 describes construction of a plasmid cloning vector, pcDNA3-IgG1, that encoded a portion of the chimeric IgG-EPOR protein used for probing phage display libraries. This plasmid vector encoded a portion of the murine IgG1 heavy chain and was designed to receive a polynucleotide cassette that encoded the ligand-binding domain of the EPOR.

EXAMPLE 1

Expression Vector Encoding the $C_{H2}$, $C_{H3}$ and Hinge Domains of the Murine IgG1 Heavy Chain A plasmid vector, pcDNA3, contains neomycin and ampicillin drug resistance (selectable marker) genes, ColE1, f1 and SV40 origins of replication, and a multiple cloning site containing restriction endonuclease recognition sequences for Hind III, Kpn I, BstX I, EcoR I, EcoR V, Not I, Xho I, Xba I and Apa I, where a DNA fragment cloned into the multiple cloning site region can be expressed by utilizing a CMV promotor contained in the vector sequence (Invitrogen Corp., San Diego Calif.). The plasmid pcDNA3 was digested with Not I and Xho I restriction endonucleases and the digestion products separated electrophoretically on a 1% agarose gel using TBE buffer (89 mM Tris, pH 8.0, 89 mM boric acid, 2 mM EDTA (ethylene diamine tetraacetic acid)). The largest DNA fragment of the digest was gel-purified, ethanol precipitated, pelleted and dried briefly. The dried pellet of purified DNA fragment was resuspended in TE buffer (10 mM Tris, pH 7.5, 1 mM EDTA) and stored at $-20°$ C. This linearized plasmid was used to receive a polynucleotide that encoded a portion of a murine immunoglobulin (Ig) heavy chain.

A polynucleotide encoding the constant region CH2, CH3 and hinge domains of the murine IgG1 heavy chain was amplified from genomic DNA using a PCR protocol employing primers having the following sequences.

First Strand Primer was (SEQ ID NO:2):
  5'-AGCTTCGA<u>GC GGCCGC</u>CGTG CCCAGGGATT GTGGTTGTAA G-3'
The opposite strand primer was (SEQ ID NO:3):
  5'-GATC<u>CTCGAG</u> TCATTACCA GGAGAGTGGG AGAGGCT-3'
The underlined portion of SEQ ID NO:2 corresponds to a Not I restriction endonuclease cleavage site, and the bolded underlined portion of SEQ ID NO:3 corresponds to an Xho I restriction endonuclease cleavage site.

Mouse genomic DNA was prepared from a lysate of frozen NIH3T3 cells using standard laboratory procedures. Briefly, cells ($5\times10^5$) were pelleted by centrifugation, washed with phosphate-buffered saline, resuspended in 100 µl of a hypotonic buffer (50 mM KCl, 10 mM Tris HCl (pH 8.4), 1.5 mM $MgCl_2$) containing 0.5% (v/v) nonionic surfactant (TWEEN® 20) and 10 µg of proteinase K. The mixture was incubated at 56° C. for 45 minutes, heated to 95° C. for 10 minutes and thereafter stored at 4° C.

The PCR reaction for amplifying the polynucleotide region encoding the CH2, CH3 and hinge domains of the murine IgG1 heavy chain was prepared by combining the following reagents in a sterile 0.6 ml microfuge tube in the following order: 10 µl of 10×PCR Buffer II (100 mM Tris HCl (pH 8.3), 500 mM KCl), 6 µl of 25 mM $MgCl_2$, 2 µl of a 10 mM solution of each dNTP, 2.5 µl of 10 nM murine IgG1 first strand primer (SEQ ID NO:2), 2.5 µl of 10 nM murine IgG1 opposite strand primer (SEQ ID NO:3), 0.5 µl (2.5 units) of a thermostable DNA polymerase (AMPLITAQ®, Perkin Elmer Corp., Foster City Calif.), 66.5 µl ultrapure water, and one wax bead. After incubating the reaction mixture at 70° C. to melt the wax bead, 10 µl of the lysate containing the genomic DNA template was added to the tube. The reaction mixture was incubated 30 cycles as follows: 1 min at 94° C., 1 min at 55° C., and 1.5 min at 72° C. (in a Perkin Elmer 480 Thermal Cycler). The completed reaction mixture was stored at 4° C. until use.

Amplified DNA from the PCR reaction was gel purified by electrophoresis through a 1% agarose gel in TBE. The band corresponding to the amplified DNA was excised from the gel and eluted in 40 µl of water. The amplified IgG1 gene fragment of about 1 kb was then digested with Not I and Xho I restriction endonucleases, and the digestion products electrophoresed on a 1% agarose/TBE gel. The about 1 kb DNA fragment was again purified from the gel and eluted in 40 µl of water. The yield of the purified fragment was determined by measuring the optical density of the solution at 260 nm (Beckman DU600 spectrophotometer).

The Xho I and Not I digested IgG1 PCR product was ligated into the Xho I and Not I digested pcDNA3 vector in a 20 µl ligation reaction containing about 100 ng each of the pcDNA3 vector and IgG1 amplified DNA fragment, in 50 mM Tris-HCl (pH 7.8), 10 mM $MgCl_2$, 10 mM dithiothreitol (DTT), 1 mM ATP, 25 µg/mL bovine serum albumin (BSA) and 1 unit of DNA ligase, incubated overnight at room temperature. A 1 µl aliquot of the ligation mix was used to transform competent *E. coli* cells (SURE® *EPICUREAN COLI®*, Stratagene, La Jolla, Calif.) according to standard laboratory procedures. Transformants were selected by growth on LB plates containing ampicillin. Plasmid DNA isolated from several independent clones was digested with Not I and Xho I and resolved on a 1% agarose/TBE analytical gel to check for the presence of the polynucleotide segment encoding the murine IgG1 constant and hinge regions. Plasmid DNA from clones containing the Not I/Xho I insert was prepared for nucleic acid sequencing.

Nucleic acid sequencing of the Not I/Xho I insert was performed using a dideoxy sequencing protocol. Sequencing reaction mixtures were run on a 4% acrylamide denaturing gels containing urea for 10 hours and the entire sequence of the fragment determined. After verifying that one of the clones, designated pcDNA3-IgG1 (SEQ ID NO:4), contained an insert having the proper sequence (i.e., murine IgG1 $C_{H2}$, $C_{H3}$, and hinge regions), a large-scale plasmid preparation was carried out.

The pcDNA3-IgG1 expression vector was used to create a new expression plasmid encoding a chimeric EPOR protein useful for probing phage display or other combinatorial libraries for ligands, as described in Example 2. It will be appreciated by those skilled in the art that the pcDNA3-IgG1 vector may be used as a recipient DNA for sequences encoding other peptides, thereby allowing one to easily create other chimeric proteins useful in similar types of probing assays. That is, the pcDNA3-IgG1 vector is a general purpose vector for producing chimeric proteins that include a portion of the murine.

The following example describes the methods used to construct a plasmid expression vector that encoded a chimeric protein having the $C_{H2}$, $C_{H3}$, and hinge regions of murine IgG1 and the ligand-binding domain of the human EPOR.

EXAMPLE 2

Expression Vector Encoding a Chimeric Receptor Incorporating the EPOR Ligand Binding Domain A DNA fragment encoding the extracellular portion of the human EPOR was obtained by PCR amplification of cDNA which had been synthesized from human leukocyte total RNA. RNA was reverse transcribed in a reaction mixture that included: 1 μg RNA, 12.5 Mm of each dNTP, 50 mM Tris-HCl (pH 8.3), 40 mM KCl, 5 mM DTT (dithiolthreitol), 20 pmoles of random deoxyribonucleotide hexamers, and 100 units of reverse transcriptase (SUPERSCRIPT®, Life Technologies Gibco/BRL, Grand Island, N.Y.). The mixture was incubated for 1 hour at 42° C., heat-treated at 95° C. for 5 minutes and then stored at 4° C. until use. PCR reactions were performed using the following primers.

The first strand primer was:
5'-GATCGGATCC<u>ATG</u>GACCACCTCGGGGCGTCC-CTC-3' (SEQ ID NO:5); and
the opposite strand primer was:
5'-AGCTTCGAGCGGCCGCGGGGTCCAGGTCG-CTAGGCGTCAG-3' (SEQ ID NO:6).

The first strand primer (SEQ ID NO:5) incorporated into the amplification product an ATG translation start codon (shown underlined above) and a Bam HI recognition sequence (shown bolded above) located immediately upstream of the start codon. The opposite strand primer (SEQ ID NO:6) introduced a Not I restriction endonuclease cleavage site (shown bolded above) at the downstream terminus of the amplified fragment.

PCR reactions were performed using conditions substantially as described in Example 1 but with the primers having the sequences of SEQ ID NO:5 and SEQ ID NO:6, and yielded an amplified EPOR DNA fragment having the sequence of SEQ ID NO:7. The amplified EPOR DNA fragment (i.e., the PCR product) and the pcDNA3-IgG1 plasmid each were digested with Bam HI and Not I, and the large DNA fragments of each reaction were gel purified using methods as described in Example 1. The purified EPOR DNA fragment and plasmid vector were then ligated, using ligation conditions substantially as described in Example 1, to yield the chimeric expression vector designated pcDNA3-IgG1-EPOR. This chimeric expression vector was transfected into competent E. coli cells using standard procedures, substantially as described in Example 1. RNA transcribed from the vector-borne CMV promoter was translated within the transfected cells to yield a fusion protein having domains corresponding to murine IgG1 and the extracellular domain (ECD) of the human EPOR. Vector construction was confirmed by diagnostic restriction digests and nucleic acid sequencing using standard methods. Large scale plasmid preparations were made from a transformed E. coli clone harboring the pcDNA3-IgG1-EPOR plasmid.

The following example describes the methods used to produce the chimeric Ig-EPOR protein encoded by the pcDNA3-IgG1-EPOR plasmid described above within eukaryotic cells. Although COS-7 host cells were used in these procedures, those skilled in the art will appreciate that a variety of other cultured cells may easily be substituted.

EXAMPLE 3

Transfection of the pcDNA3-IgG1-EPOR Construct and Expression of the Chimeric Ig-EPOR Protein COS-7 cells were propagated in Dulbecco's Modified Eagle Medium (DMEM) supplemented with 4500 mg/L D-glucose, 584 mg/ml L-glutamine, and 10% fetal bovine serum (FBS). In preparation for transfections, cells were seeded at about $2-4\times10^5$ cells per T-150 in about 20 ml volumes and grown in a humidified incubator at 37° C. in a 5% $CO_2$ atmosphere until about 50% to 70% confluent. Plates were washed with serum-free media, and a mixture of 10 μg of pcDNA3-IgG1-EPOR plasmid DNA and 31 μl of standard transfection reagent comprising positively charged and neutral lipids (LIPOFECTAMINE®, GibcoBRL, Grand Island, N.Y.) in DMEM was added to the cells, which were then returned to the incubator for 5 hrs. Transfection media subsequently was replaced with DMEM and 10% FBS. Stable transfectants were drug selected in the presence of G418 using standard laboratory procedures. After 48 to 72 hrs, cell free media was assayed for the presence of the Ig-EPOR protein using an ELISA protocol described in the following example. The results of those assays showed that proteins in the cell free supernatants contained one moiety capable of binding to authentic EPO and another moiety capable of binding to an anti-IgG antibody. That is, transfectants containing the pcDNA3-IgG1-EPOR plasmid expressed a chimeric protein that included functional IgG1 and EPOR regions.

Example 4 describes the ELISA methods used to confirm that the chimeric Ig-EPOR protein was secreted from cells transfected with the pcDNA3-IgG1-EPOR plasmid and describes the method used to demonstrate that the chimeric protein simultaneously could bind authentic EPO and a labeled anti-IgG antibody.

EXAMPLE 4

ELISA Protocol to Verify the Production and Integrity of the Chimeric Ig-EPOR Protein
(1) Relative Quantities of Secreted Proteins The wells of a standard 96-well plate (IMMULON®2, Dynatech) were coated with goat anti-murine IgG$_{fc}$ that hAd been diluted 1/1,000 in PBS. After blocking the wells for nonspecific binding using a solution of 1% BSA and 0.05% TWEEN® 20 in PBS, serially diluted samples of the cell free supernatant from transfectants were added to the wells and allowed to contact the immobilized antibody. After removing unbound chimeric protein by washing, a horseradish peroxidase (HRP) labeled anti-murine IgG1 detection antibody was added and allowed to bind the IgG portion of the chimeric protein. The HRP labeled antibody, bound to the chimeric protein, was detected using a TMB peroxidase substrate (Kirkegard & Perry, Gaithersburg Md.) using standard procedures. Activities were calculated by spectrophotometric measurements at 450 nm to 650 nm. That is, the concentration of the chimeric protein was calculated relative to a standard curve of known antibody. Specifically, absorbance of each dilution at 450 nm was measured and the absorbance at 650 nm was subtracted to eliminate absorbance from non-specific sources (e.g., cell debris and dust).

Results of these procedures indicated that protein concentrations ranged from 125 to 4,000 ng/ml depending on the confluency of the culture and the frequency of supernatant harvesting.

Having confirmed that transfected cells secreted a protein having a domain identifiable with anti-murine IgG antibodies, we proceeded to verify that the chimeric protein also could bind the EPO ligand.

(2) EPO-Binding Activity of the Chimeric Receptor

The wells of a 96-well microliter plate were coated with a 3.1 unit/ml solution of recombinant human EPO (R & D Systems, Minneapolis Minn.) that had been diluted in PBS. The wells were washed three times with PBS containing 0.05% (v/v) TWEEN® 20 non-ionic detergent, and then blocked with 1% (w/v) BSA and 0.05% TWEEN® 20 in PBS (blocking buffer) to prevent non-specific binding. Excess blocking buffer was removed by washing once. Culture media was serially diluted in blocking buffer, and 50 µl from each dilution was added to the coated and blocked wells. Wells receiving undiluted media served as a control. A set of uncoated wells also received the diluted cell-free media. Plates were then incubated for 2 hours at room temperature, and washed three times as described above. After removing unbound chimeric receptor by washing, bound chimeric protein was assayed using 100 µl of the HRP labeled anti-murine IgG antibody, substantially as described above. Color development was initiated by addition of 100 µl of the TMB peroxidase substrate, and the extent of the peroxidase reaction measured spectrophotometrically at 450 nm and 650 nm, as described above.

Results of these procedures indicated that the chimeric receptor protein bound to EPO, and was detectable by using a labeled anti-murine IgG antibody. Control wells showed no color development, whereas wells in which an EPO/Ig-EPOR complex had been formed were distinctly blue to purple in color.

These results showed that the chimeric IgG-EPOR protein was suitable as a probe for identifying EPOR ligands. That is, the chimeric Ig-EPOR exhibited specific binding to EPO, and also specifically bound an anti-murine IgG antibody.

The following example describes the methods used to purify the chimeric Ig-EPOR protein used to identify EPOR ligands.

EXAMPLE 5

Purification of the Chimeric Ig-EPOR Protein

Sterile culture supernatants containing the chimeric receptor protein were loaded onto an anti-murine IgG1 affinity column (SEPHAROSE® affinity column, Zymed Laboratories, San Francisco Calif.) equilibrated with PBS. After loading, the column was washed with phosphate-buffered saline solution (PBS) to remove non-specifically bound proteins. Proteins bound to the anti-IgG1 were removed from the column by eluting with a buffer containing 0.15 M NaCl and 0.1 M glycine (pH 2.4). Protein-containing fractions were pooled, concentrated and buffer exchanged into PBS using standard procedures (CENTRICON® 50 cartridge, Amicon, Beverly, Mass.). The relative protein concentration of the Ig-EPOR chimera was determined using an IgG sandwich ELISA and a known concentration of antibody, all according to standard laboratory procedures substantially as described in Example 4. The integrity of the chimeric protein was determined by PAGE on 4% to 20% Tris-glycine pre-cast acrylamide gels and silver staining (Bio-Rad, Hercules Calif.), and immunoblotting using HRP labeled goat anti-murine IgG1 to detect the Ig-EPOR protein, also according to standard laboratory procedures.

Results of these procedures indicated that the major protein species had a molecular weight of about 59 KDa. Contaminating bands and degradation products on the gel were minimal. Binding kinetics investigated by Biacore analysis were in good agreement with known affinity values ($0.1–1.1\times10^{-9}$ k) (Karlsson et al., 1991, *J. Immunol. Methods* 145 (1–2):229–240). The Ig-EPOR protein easily was recoverable in microgram amounts using the procedures described above.

Using this purified chimeric Ig-EPOR protein as a probe, we isolated a phage clone that bound the EPOR by screening phage display libraries. The protein probe was immobilized to magnetic beads, although alternative solid supports could readily be used. The magnetic beads were employed because the high surface area of the matrix facilitated efficient contact between the immobilized probe and phage, and magnetic separation allowed efficient washing between processing steps.

Example 6 describes the methods used to isolate recombinant phage that expressed fusion proteins capable of binding the chimeric Ig-EPOR probe

EXAMPLE 6

Biopanning Methods and Magnetic Bead ELISA

Four M13 phage display libraries which expressed random peptides as a pIII fusion protein were screened independently using biopanning with the Ig-EPOR probe. These libraries, designated XC8, XC13, X38, XC43, were constructed using previously described procedures (McConnell et al., *Molec. Diversity* 1:165–176, 1996). The XC8 and XC13 libraries displayed random amino acid sequences of 8 and 13 residues, respectively, flanked by cysteine residues. The XC38 library expressed a fusion protein displaying 37 random amino acids surrounding an invariant alanine at position 22 in the peptide sequence. The XC43 library displayed 43-mer peptides comprising 40 random amino acids surrounding an invariant Gly-Cys-Gly sequence at residues 21, 22 and 23, which allows the potential for a displayed peptide to form an intramolecular disulfide loop.

The phage libraries were screened for EPOR binding clones using the above-described chimeric Ig-EPOR protein as a probe using standard biopanning procedures. Biopanning was performed using the chimeric receptor protein immobilized to magnetic beads (DYNABEADS® M45 rat anti-murine IgG1 beads, Dynal, Inc.) using standard procedures. Chimeric Ig-EPOR protein (500 ng/ml) contained in 10 ml of cleared supernatant from cells transfected with the pcDNA3-IgG1-EPOR plasmid was combined with 400 µl of magnetic beads, and the mixture incubated at 4° C. overnight with gentle shaking. Beads were subsequently blocked for 1 hr at room temperature in standard Tris-buffered saline blocking medium (TBS SUPERBLOCK®, Pierce Chemical, Chicago Ill.). Beads were further treated by addition of the Fc fragment of murine IgG (10 μg/ml), for 1 hr at room temperature to block high affinity sites that could non-specifically bind the IgG domain of the chimeric probe. The beads were washed three times in TBST (Tris buffered saline containing 0.1% (v/v) TWEEN® 20) and then suspended in 1 ml blocking medium (TBS SUPERBLOCK®). Phage in 100 μl aliquots containing about $1 \times 10^{10}$ plaque forming units (pfu) were added to the beads and the mixtures rotated gently for 2 hrs at room temperature. After washing the beads five times in TBST, phage were eluted with 300 μl of 50 mM glycine buffer (pH 2.2) for 10 min at room temperature. Eluted phage were immediately neutralized with 8 μl 2M Tris base that had not been pH-adjusted, mixed and stored at 4° C. Phage isolated by biopanning were amplified by mixing equal volumes of eluted phage and an overnight culture of E. coli strain JS5, diluting the mixture in 20 ml 2xYT containing tetracycline (12.0 μg/ml), and incubating overnight with shaking at 37° C. The resulting phage lysates were cleared of cell debris by centrifugation for 5 min in a microfuge, and 100 μl of the resulting supernatant lysate was used for a subsequent round of biopanning. All phage titering was carried out using JS5 bacteria plated on 2xYT top agar and agar plates.

Results of the library screening procedure indicated that a phage clone isolated from one of the four libraries bound the chimeric Ig-EPOR probe. This clone, designated ERB1 (for "EPO receptor binder 1"), harbored DNA encoding a pIII fusion protein that bound to the probe. The ERB1 clone included a polynucleotide having the sequence of SEQ ID NO:8 fused to sequences encoding the pIII coat protein. The amino acid sequence of the EPOR-binding peptide contained within the ERB1 clone was:

DFDVCRRGWVGHCKDWLSDEYAS-NPSYPVPHSYYLNPP (SEQ ID NO:9).

Although the amino acid sequence of the ERB1-encoded peptide was unrelated to the amino acid sequence of EPO, the ERB1 phage clone bound specifically to the Ig-EPOR protein.

A magnetic bead ELISA protocol was used to verify that the ERB1 phage clone bound to the chimeric Ig-EPOR probe by specific interactions. The chimeric Ig-EPOR probe was bound to magnetic beads displaying rat anti-murine IgG1, substantially as described above. Samples (100 μl) of 1:2 serial dilutions (PBS and 1% BSA) of a phage lysate were combined with the beads, and the phage allowed to bind the immobilized probe for 1 hr at room temperature. Phage used in this procedure were ERB1 and two negative control phage: HPKF, a clone that binds specifically to a commercially obtained anti-IL-8 mAb, and IL6-B26, a clone that binds specifically to a human IL-6 receptor. After removing unbound phage by washing four times with 200 μl aliquots of TBST (25 mM TrisHCl, pH 7.2, 0.15 M NaCl, 0.1% TWEEN® 20), an HRP-conjugated anti-M13 detection antibody (Pharmacia) diluted 1:5,000 in PBS was added. After incubating (1 hr at room temperature), excess detection antibody was removed by washing and 10 μl for each of the washed bead complexes was transferred to microtiter wells (FALCON® 3912, MICROTEST III, Beckton Dickinson, Oxnard, Calif.) that served as reaction vessels. Each well was developed using the TMB peroxidase substrate and the extent of the peroxidase reaction measured spectrophotometrically, as described in Example 4.

The results presented in FIG. 1 showed that the ERB1 phage clone and the Ig-EPOR probe interacted specifically. The inverse relationship between the optical density (O.D.) readout in the ELISA assay and the extent of phage dilution showed that progressively more dilute samples of the ERB1 phage resulted in correspondingly less binding of the anti-M13 detection antibody. Control procedures indicated that the ERB1 clone did not bind to the magnetic beads alone, or to the extracellular domains of the receptors for tumor necrosis factor (TNFR) or interleukin-6 (IL-6R) (results not shown). Moreover, control phage, having specificity either for an anti-IL-8 mAb or for the IL-6 receptor, showed no binding to the Ig-EPOR probe. Thus, the ERB1 clone bound specifically to the Ig-EPOR probe.

We also verified that interactions between the Ig-EPOR probe and the ERB1 phage clone involved the ligand binding domain of the probe. To make this determination, magnetic beads were first coated, using substantially the procedures described above, with the chimeric Ig-EPOR protein or a negative control which was a chimeric Ig-IL-6 receptor protein (described by Brown et al., 1997, "A versitile expression system for the extracellular domain of Type I cytokine receptors" (submitted for publication)). About $1 \times 10^8$ pfu of ERB1 and IL6-B26 phage clones were independently mixed with increasing amounts of EPO, and the mixtures contacted with the coated beads. After washing to remove unbound phage and EPO, the HRP-conjugated anti-M13 detection antibody was added to all samples and incubated (1 hr, room temperature) and then excess detection antibody was removed by washing. The washed bead complexes (10 μl) were transferred to 96-well microtiter wells, developed using the TMB peroxidase substrate, and the reaction measured spectrophotometrically, substantially as described above.

Figure 2:
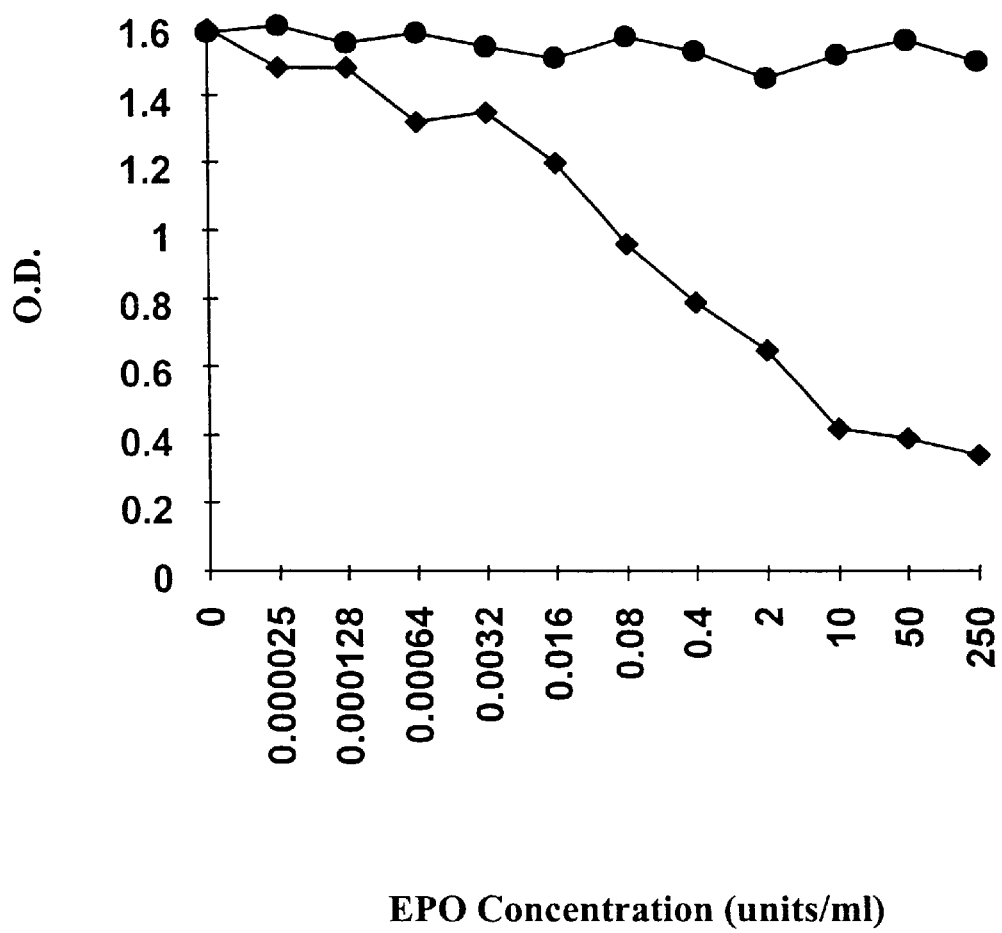
FIG. 2 is a line graph showing the results of an ELISA (O.D.) in which recombinant EPO at different concentrations (Units/ml) competed with the ERB1 phage ( ) for binding to Ig-EPOR, but had no effect on a phage ( ) that bound to the IL-6 receptor.
Figure 5A:
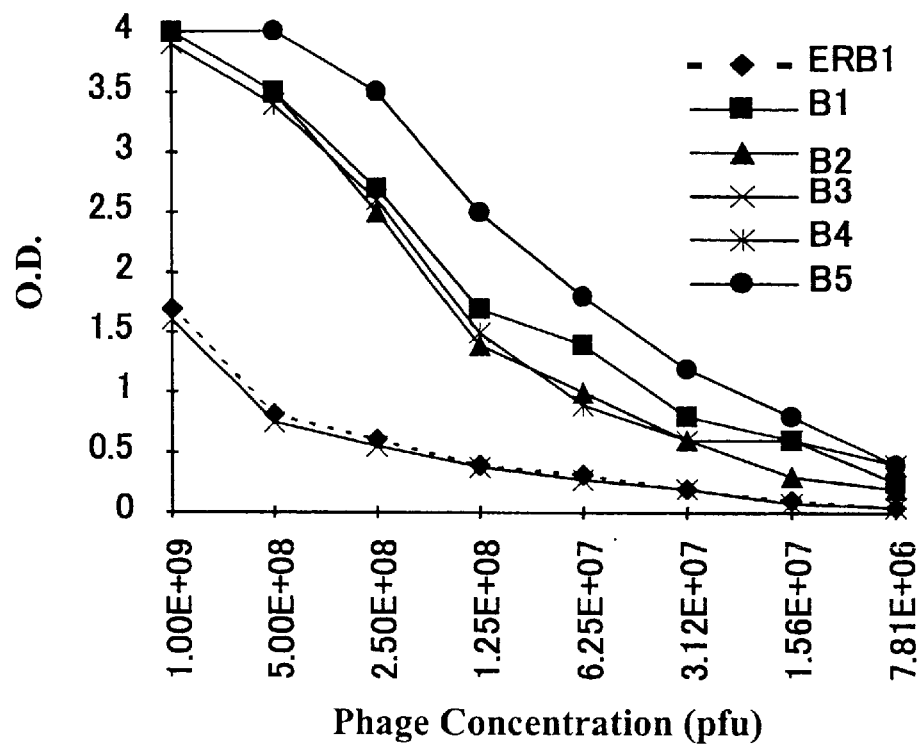
FIGS. 5A to 5D are a series of line graphs showing the affinities of several independent phage clones for the Ig-EPOR, relative to the original ERB1 isolate.
Figure 5B:
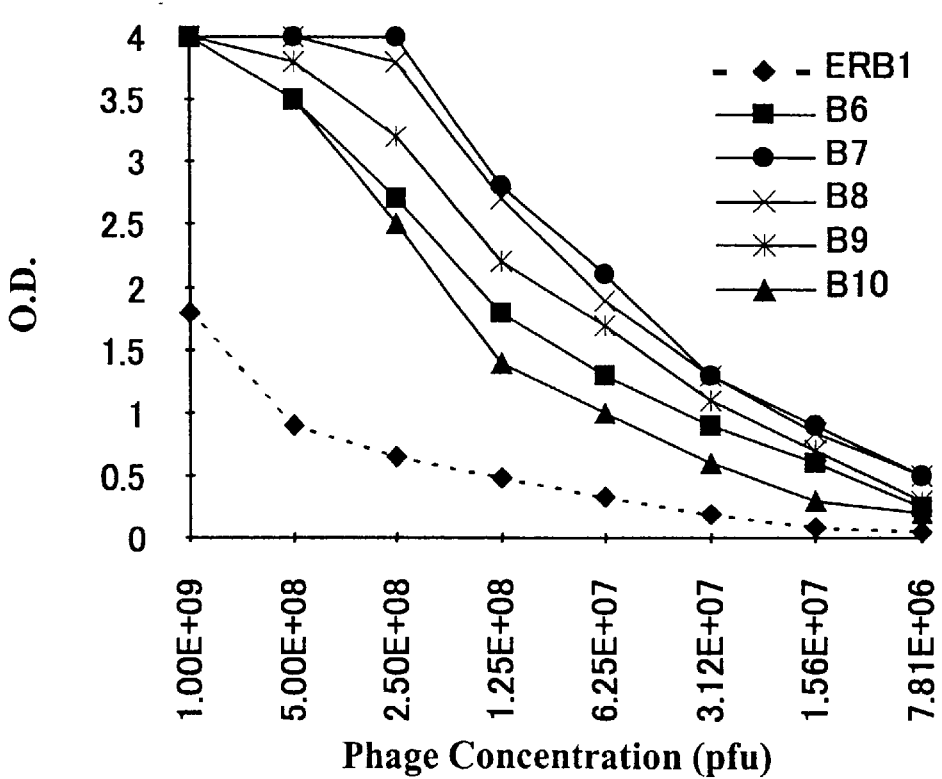
Figure 5C:
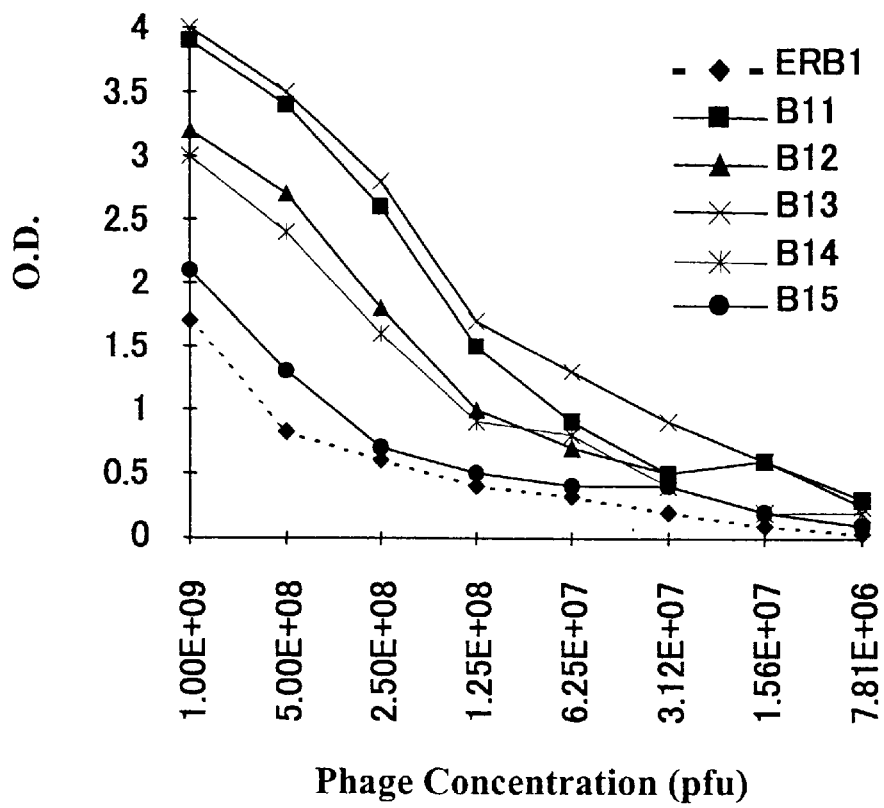
Figure 5D:
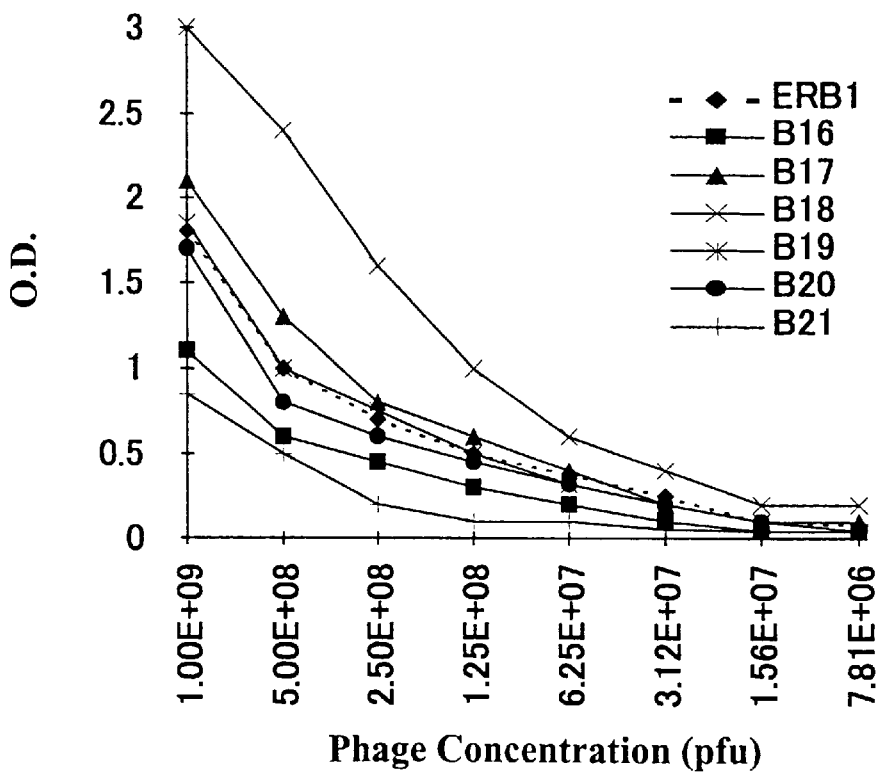

The results presented in FIG. 2 confirmed that the ERB1 phage clone and EPO both bound to the ligand binding domain of the Ig-EPOR probe. The results showed that increasing concentrations of EPO competed with ERB1 for binding to the probe. Increasing the concentration of EPO decreased the number of ERB1 phage clones that bound to the probe. Increasing concentrations of EPO did not inhibit binding of an unrelated phage/probe combination. Thus, the interactions between the ERB1 phage clone and the Ig-EPOR probe were specific and could be competed by the authentic EPO ligand. Moreover, the chimeric Ig-EPOR probe described herein represented the binding characteristics of the EPOR and molecules that bound the chimeric probe would be expected to bind to EPOR.

To obtain phage clones having similar or higher affinity for the EPOR than the ERB1 clone, and to identify subsequences within the ERB1 fusion protein that contributed to EPOR binding, an evolved library was created using saturation oligonucleotide doping mutagenesis of the original ERB1 sequence and the evolved library was screened using the chimeric Ig-EPOR probe. The following example describes the methods used to create and screen a phage display library of 38-mer peptides that were related to the fusion protein expressed by the ERB1 phage clone.

EXAMPLE 7

Construction and Screening of an ERB1 Evolved Library

An evolved library was constructed using procedures substantially as described previously (McConnell et al., 1996, *Molecular Diversity* 1:165). Briefly, we synthesized a collection of oligonucleotides such that codons corresponding to each amino acid position of the 38-mer ERB1 EPOR-binding peptide were independently substituted by random amino acids at a predetermined frequency, except for the DEY internal amino acid sequence near the center of the ERB1 sequence. Using these procedures, codons representing substitutions of random amino acids at any single position in the 38-mer peptide, except those encoding the DEY tripeptide, were predicted to occur at a frequency of approximately 50%.

Polynucleotides were synthesized according to the doping scheme diagramed in FIG. 3. Briefly, two collections of redundant oligonucleotides, represented by the oligonucleotides of FIG. 3A (SEQ ID NO:10 and SEQ ID NO:11), were synthesized so that oligonucleotides of the two groups could be annealed to each other using short complementary sequences present at their 3' ends. These complementary sequences encode the internal D-E-Y amino acids of the ERB1 peptide, thus maintaining this tripeptide in each of the clones of the resulting evolved library. The complementary strands of the population of annealed oligonucleotides were then synthesized by standard in vitro DNA extension methods to create a population of double-stranded DNA fragments. These DNA fragments were cloned into an appropriate M13 vector (e.g., MSM1 of McConnell et al., supra) to produce a phage display library that expressed pIII fusion proteins, where each fusion protein includes an N-terminal 38-mer peptide derived from the ERB1 peptide sequence. For the first two positions of each codon of the ERB1 oligonucleotide, the redundant oligonucleotides were synthesized using 73% of the nucleotide identical to the nucleotide used in that position of the ERB1 oligonucleotide sequence and 9% of the other three nucleotides. The nucleotide compositions that correspond to each base shown in lower case in the redundant oligonucleotide sequences are shown in FIG. 3B. The third position of each codon (represented by "s" in FIGS. 3A and 3B) was synthesized using an equimolar mixture of dGTP and dCTP. This doping scheme produced nucleotide triplets encoding the original amino acid at each position of the ERB1 38-mer peptide approximately 50% of the time. The remaining 50% of the time, codons that did not encode the original amino acid were substituted by a random mixture of the other 19 amino acids.

The resulting ERB1 evolved library was screened by biopanning substantially as described in Example 6 to identify clones that bound the chimeric Ig-EPOR probe. Several random phage clones also were isolated from the evolved library, to represent non-binding clones. As judged by the results of EPOR-specific magnetic bead ELISA testing (as described in Example 6), approximately 88% of clones selected from the panned group were positive for EPOR binding, whereas all of the randomly selected clones from the unpanned group were negative for EPOR binding. This indicated that randomly selected clones in the evolved library were unlikely to bind the EPOR, whereas clones selected by the panning procedure exhibited EPOR binding at a very high frequency. Thus, the screening methods described herein are useful for identifying and isolating phage clones that exhibit ligand functionality; in this case, clones capable of binding to EPOR.

A total of 48 binding (panned group) and 24 non-binding (unpanned group) clones were isolated from the evolved library. DNA sequences encoding the 38-mer regions of the fusion peptides these clones were determined by dideoxy sequencing using standard procedures. Among these 72 isolates, 34 unique sequences were found (21 sequences for the panned group and 13 sequences for the unpanned group). These 34 unique DNA sequences are disclosed in SEQ ID NO:13 to SEQ ID NO:46 and the predicted amino acid sequences encoded by these sequences are disclosed in SEQ ID NO:47 to SEQ ID NO:80. The peptide sequences are shown in FIG. 4. A total of 21 different binding clones, designated B1 to B21 (SEQ ID NO:47 TO SEQ ID NO:67), were isolated from the originally selected 48 binding clones; and 13 different non-binding clones, designated as N1 to N13 (SEQ ID NO:68 to SEQ ID NO:80), were isolated from the originally chosen 24 non-binding clones.

From the aligned peptide sequences of the EPOR binding and non-binding clones, a consensus sequence present in all binding clones and absent in non-binding clones was determined. Excluding the DEY tripeptide which was present in all of the clones due to the mutagenic scheme used (see FIG. 3A), the consensus sequence was CXXGWVGXCXXW (SEQ ID NO:12), where the X's represent positions tolerant of variable amino acids. The invariant residues in the consensus sequence found in the binding clones is shown in bold in FIG. 4. In non-binding clones, some invariant residues were also present (underlined in FIG. 4), but the complete motif of the consensus sequence was not present. Because binding and non-binding clones all included the same pIII protein sequences, binding of the phage clones to the EPOR probe was not due to interaction between the probe and pIII sequences. Instead, binding of the phage clones to the Ig-EPOR probe must have been due to the presence of additional peptide sequences of the fusion protein (e.g., those shown for clones B1 to B21 in FIG. 4). Thus, peptides that included the 12-mer consensus sequence bound to the ligand binding domain of the human EPOR and peptides comprising the sequence of SEQ ID NO:12 represented EPO peptide mimetics.

To better characterize the phage isolates having binding specificity for the EPOR, we compared the relative affinities of the binding clones presented in FIG. 4, using a phage ELISA procedure. Phage stocks of the binding clones were titered in triplicate to accurately determine the concentration of pfu/ml for each lysate. Different isolates were then assayed by ELISA using normalized phage concentrations so that all clones were tested using equivalent numbers of phage. Optical densities in the ELISA corresponding to the equivalent of a 50% maximum response in the ERB1 trial were next determined for each of the different phage isolates. The optical density per phage at 50% ERB1 maximum response multiplied by $1 \times 10^8$ gave a value of 1.0 for ERB1, and represented the standard for measuring relative binding affinity of the B1 to B21 isolates. The normalized relative affinity ("Rel. Aff.") for each clone is shown to the right of the clone's peptide sequence in FIG. 4. For each of the non-binding clones, the relative affinity is listed as <0.1 because each of these was negative for EPOR binding.

FIGS. 5A–5D graphically show the ELISA results of clones B1 to B2. Several clones, including B7 and B8, bound the chimeric Ig-EPOR protein with affinities about 20-fold higher than the affinity of the parent ERB1 clone. Other clones, including B3, B15 and B19, bound the EPOR with affinities similar to ERB1 and two clones (B20 and B21) had somewhat lower binding affinities compared to ERB1. The different relative affinities probably result from amino acid differences between the different clones. Thus, many binding clones isolated from the evolved library bound to the ligand binding domain of the human EPO receptor with increased affinities relative to that the ERB1 parent clone. All of the binding clones had peptides that included the 12-mer consensus sequence identified by SEQ ID NO:12.

The following example describes methods used to demonstrate that synthetic peptides having amino acid sequences derived from the sequences of the binding clones described above competed with authentic EPO for binding to Ig-EPOR.

EXAMPLE 8

Peptide Inhibition ELISA

This example shows that synthetic peptides that include the consensus sequence of SEQ ID NO:12 competed with EPO for EPOR binding. Because the consensus sequence was positioned on the amino-terminal side of the conserved DEY residues, peptides were synthesized based on the amino-terminal sequences of two exemplary clones that exhibited high affinity binding for the chimeric Ig-EPOR probe. The peptides were synthesized in the cyclic form and include sequences corresponding to the amino-terminal 18 amino acids of the B7 and B8 clones.

Figure 6:
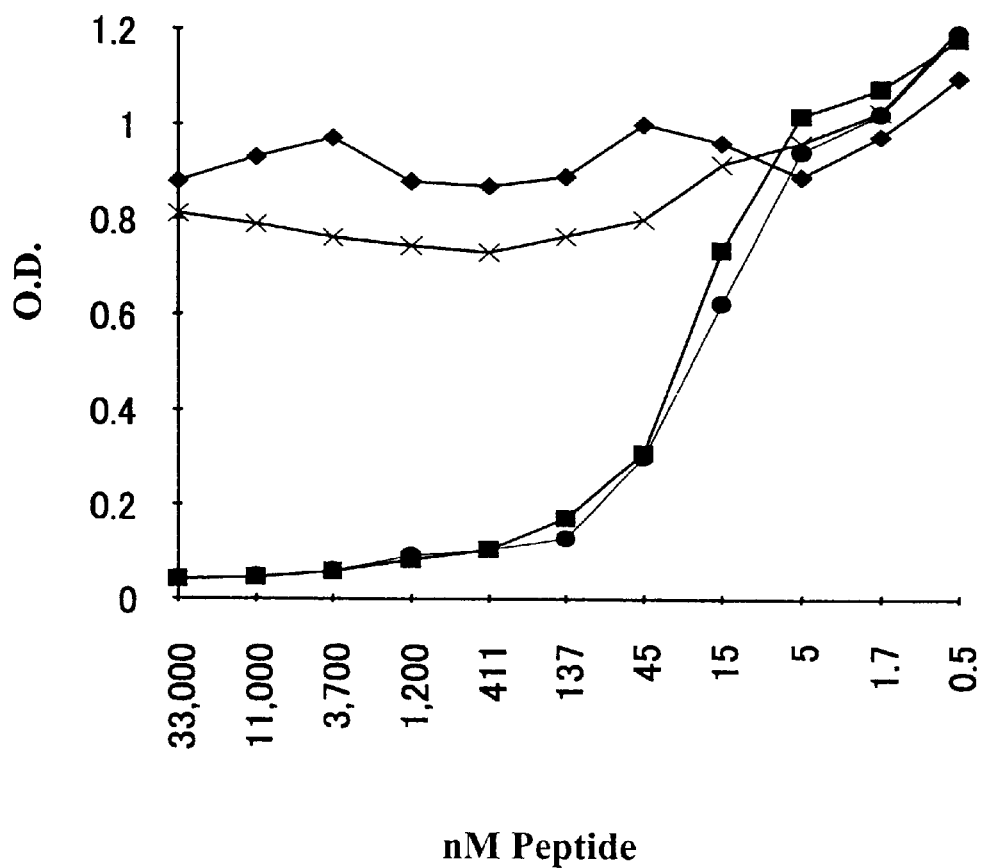
FIG. 6 is a line graph showing the results from a peptide inhibition ELISA in which binding of the chimeric Ig-EPOR probe to immobilized EPO was inhibited by competitor peptides (peptide ERB1-7,; peptide ERB1-8,) compared to no peptide added ( ) or addition of an irrelevant peptide that binds to IL-6 receptor (x).

Synthetic peptides having the sequences DREGCRRG-WVGQCKAWFN (SEQ ID NO:81), and DVEACGGG-WVGHCNYWLR (SEQ ID NO:82) were synthesized in the cyclic (disulfide-bonded) form using standard procedures (Peninsula Laboratories, Belmont, Calif.). The 18-mer peptide sequences were derived from the B7 and B8 clones, and the peptides are referred to herein as "ERB1-7" (SEQ ID NO:81) and "ERB1-8" (SEQ ID NO:82), respectively. The structures of the two purified peptides, each being greater than 95% pure as judged by HPLC, were confirmed by mass spectrometry. The peptides were tested separately in the EPO specific sandwich ELISA protocol described above for their ability to inhibit binding of the Ig-EPOR protein to EPO-coated polystyrene plates. The results presented in FIG. 6 show that both the ERB1-7 and ERB1-8 synthetic peptides competed with EPO for binding to the chimeric Ig-EPOR protein. Both peptides had $IC_{50}$ values of about 45 nM in the assay. This proved that synthetic 18-mer peptides derived from the sequences of the binding clones (see FIG. 4), that included the consensus 12-mer sequence identified above, bound the EPOR even when removed from the context of the M13 pIII fusion protein. These results support the conclusion that 18-mer peptides that include the consensus 12-mer sequence (SEQ ID NO:12) and four amino acids on the amino-terminal side and two amino acids on the carboxyl-terminal side of the consensus sequence are EPOR binding compositions. Such synthetic peptides are EPO mimetics.

To identify the size limits of functional EPO peptide mimetics, shorter forms of ERB1-7 were synthesized and tested to determine the relationship of peptide size and receptor binding activity. As described in the following example, a series of N-terminal truncations of ERB1-7 were synthesized and tested in the EPO specific inhibition ELISA described above.

EXAMPLE 9

Residues Outside the 12-mer Consensus are Required for High Affinity Interaction Between Synthetic

Peptides and the EPOR

This example shows that amino acid residues located outside the limits of the above-identified 12-mer consensus sequence contribute to the ability of synthetic peptides to bind the Ig-EPOR probe. Synthetic peptides corresponding to the sequence of ERB1-7, but missing either one, two, three or four N-terminal amino acids were tested in the peptide inhibition ELISA protocol. The following peptides were synthesized and tested substantially as described in Example 8: 18-mer peptide ERB1-7, consisting of DREGCRRGWVGQCKAWFN (SEQ ID NO:81);

17-mer peptide 7N-1, consisting of REGCRRG-WVGQCKAWFN (SEQ ID NO:83);

16-mer peptide 7N-2, consisting of EGCRRGWVGQCK-AWFN (SEQ ID NO:84);

15-mer peptide 7N-3, consisting of GCRRGWVGQCK-AWFN (SEQ ID NO:85); and 14-mer peptide 7N-4, consisting of CRRGWVGQCK-AWFN (SEQ ID NO:86).

Figure 7:
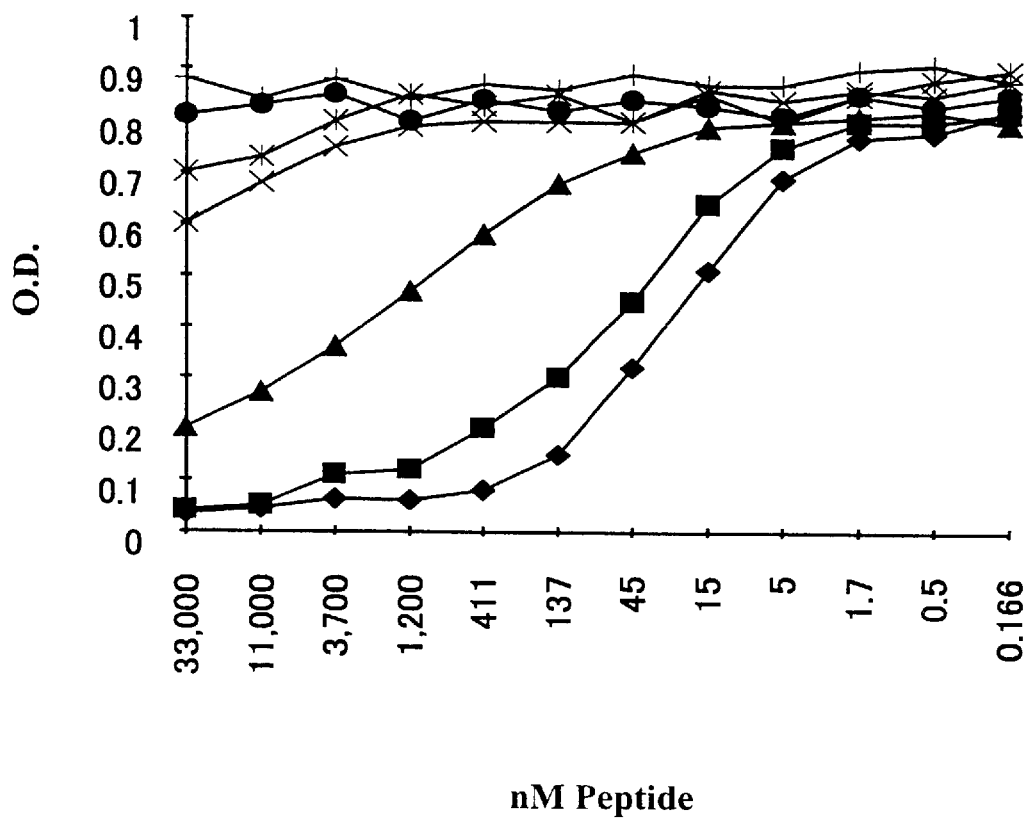
FIG. 7 is a line graph showing binding of the ERB1-7 18-mer peptide ( ) to Ig-EPOR and compared to binding to Ig-EPOR of N-terminal truncated ERB1-7 peptides (17-mer,; 16-mer,; 15-mer, x; 14-mer,), and compared to addition of an irrelevant peptide that binds to IL-6 receptor ( ) or no inhibitor added ( ).

The results presented in FIG. 7 show that amino acids in addition to the 12-mer consensus contributed to effective competition with EPO for binding to the Ig-EPOR protein. That is, the $IC_{50}$ of value for 18-mer was approximately 45 nM, whereas the 17-mer peptide showed a decreased $IC_{50}$ of 91 nM. Further truncation produced the 16-mer that had an $IC_{50}$ of about 3700 nM. Further truncations (i.e., to 15-mer and 14-mer peptides) abolished EPOR binding activity. Truncation of the ERB1-7 peptide not only compromised the physical interaction between the peptide and Ig-EPOR, but also compromised the peptide's biological activity, as described in Example 10. Thus, the consensus 12-mer peptide sequence given by SEQ ID NO:12 likely was necessary but not sufficient to create synthetic peptides having high affinity for the EPOR.

The following example describes the methods used to demonstrate that synthetic peptides which bound the EPOR also exhibited EPO-like pharmacological activity in an in vitro cell culture system.

EXAMPLE 10

ERB1 and Evolved Peptides Stimulate Proliferation in EPO-Responsive Cell Lines To evaluate the biological activities of two representative synthetic peptides containing the 12-mer consensus sequence, peptides ERB1-7 and ERB1-8 were tested for their ability to stimulate proliferation of the EPO-responsive cell line (TF-1). Those having ordinary skill in the art will appreciate that the TF-1 cell line is useful for detecting and quantitating EPO biological activity, although other EPO-responsive cells could be substituted. The TF-1 cell line was established from a heparinized bone marrow aspirate isolated from a 35-year-old male exhibiting pancytopenia (Kitamura et al., 1989, *J. Physiol.* 140:323).

TF-1 cells were propagated in RPMI 1640 containing 10% BCS and 5 ng/ml GM-CSF. After washing twice with PBS to remove residual GM-CSF, 5,000 cells were placed in each well of a 96-well microtiter plate in the presence of 0.5 units EPO/ml and cultured for three days under standard conditions (Kitamura et al., 1989, *Blood* 73:375–380). Proliferation in response to EPO was determined using a standard XXT assay (assay based on sodium 3'-(-1-(phenylaminocarbonyl)-3,4-tetrazolium)-bis (4-methoxy-6-notro) benzene sulfonic acid hydrate; Promega, Madison Wis.). Similar procedures were followed using the ERB1-7 (SEQ ID NO:81) or ERB1-8 synthetic peptide (SEQ ID NO:82) instead of EPO. Also tested as a negative control was an IL-6 peptide having the sequence GGAFCEAVGCG-PDRNFYGG (SEQ ID NO:87). Peptide concentrations were tested over a 1,000-fold concentration range of 0.02 to 20 $\mu$M.

Figure 8A:
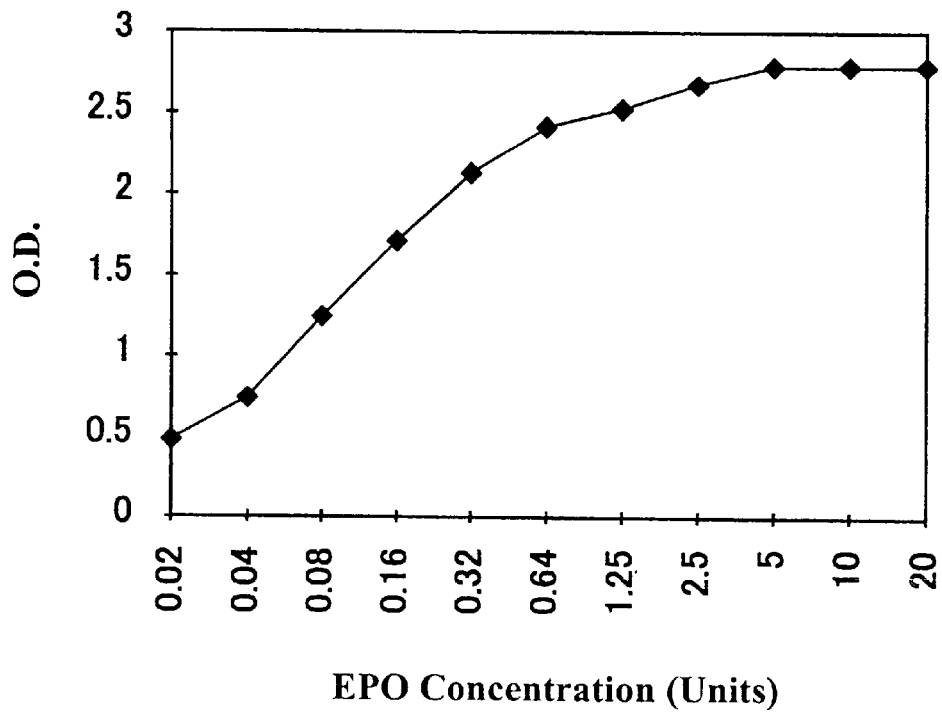
FIGS. 8A and 8B are line graphs showing the results from a TF-1 cell proliferation assays.
Figure 8B:
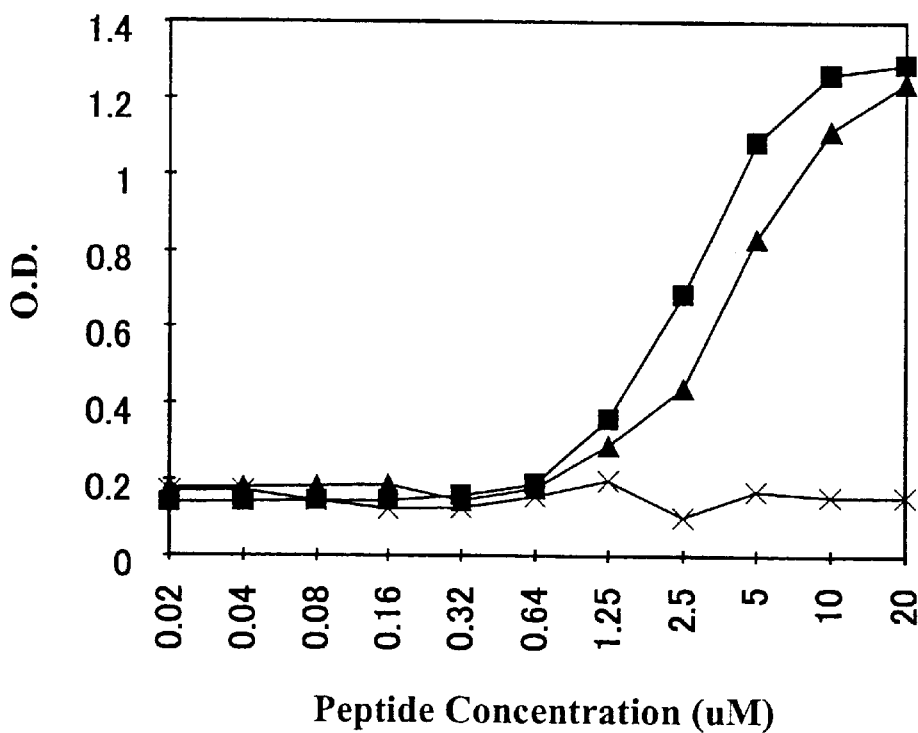

The results presented in FIGS. 8A and 8B show that the synthetic peptides which bound the EPOR also exhibited EPO-like pharmacologic activity in a biological assay. The positive control, purified EPO, confirmed that the TF-1 cells were EPO responsive. The TF-1 cells proliferated with a half maximal response (ED$_{50}$) in the range of 0.05 to 0.1 unit/ml of EPO (FIG. 8A). Both peptides were EPOR agonists, producing proliferative responses in a dose-dependent manner in TF-1 cells at concentrations from 1 to 10 µM (FIG. 8B). In contrast, an irrelevant IL-6 peptide that did not bind the EPOR did not stimulate TF-1 cell proliferation at any tested concentration up to 20 µM. This showed that nonspecific interactions in the assay did not contribute to the proliferative results seen with the synthetic EPO mimetics. Thus, synthetic peptides that included the consensus 12-mer of SEQ ID NO:12 and flanking amino acids exhibited a biological activity similar to EPO. While particular embodiments of the invention have been described in detail, it will be apparent to those skilled in the art that these embodiments are exemplary rather than limiting, and the true scope of the invention is defined by the claims that follow.

What is claimed is:

1. A isolated polypeptide capable of binding to a human erythropoietin receptor, said isolated polypeptide selected from the group consisting of:

$X_{n1}$-$X_{n2}$-C-$X_1$-$X_2$-G-W-V-G-$X_3$-C-$X_4$-$X_5$-W-$X_{c1}$-$X_{c2}$ SEQ ID NO. 88;

$X_{n1}$-$X_{n2}$-$X_{n3}$-C-$X_1$-$X_2$-G-W-V-G-$X_3$-C-$X_4$-$X_5$-W-$X_{c1}$-$X_{c2}$ SEQ ID NO. 89; and $X_{n1}$-$X_{n2}$-$X_{n3}$-$X_{n4}$-C-$X_1$-$X_2$-G-W-V-G-$X_3$-C-$X_4$-$X_5$-W-$X_{c1}$-$X_{c2}$ SEQ ID NO. 90 wherein, $X_{n1}$-$X_{n2}$-$X_{n3}$, or $X_{n1}$-$X_{n2}$-$X_{n3}$, or $X_{n1}$-$X_{n2}$-$X_{n3}$-$X_{n4}$ are N-terminal peptides selected from peptides of from 2 to 4 natural α-amino acids in length comprising $X_{n1}$-$X_{n2}$, or $X_{n1}$-$X_{n2}$-$X_{n3}$, or $X_{n1}$-$X_{n2}$-$X_{n3}$-$X_{n4}$, respectively; $X_1$, $X_2$, $X_3$, $X_4$ and $X_5$ are independently selected from the group consisting of natural α-amino acids; and $X_{c1}$-$X_{c2}$ is a C-terminal dipeptide.

2. The isolated polypeptide of claim 1, wherein $X_n$ is $X_{n1}$-$X_{n2}$-$X_{n3}$-$X_{n4}$ wherein $X_{n1}$ is selected from the group consisting of neutral and polar, neutral and hydrophobic, and acidic natural α-amino acids, or optionally $X_{n1}$ is absent;

$X_{n2}$ is selected from the group consisting of neutral and polar, neutral and hydrophobic, and basic natural α-amino acids, or optionally $X_{n2}$ is absent if $X_{n1}$ is absent;

$X_{n3}$ is selected from the group consisting of natural α-amino acids; and $X_{n4}$ is selected from the group consisting of neutral and polar, neutral and hydrophobic, and acidic natural α-amino acids.

3. The isolated polypeptide of claim 2, wherein $X_{n1}$ is E, G, N, S, D, Q, L, Y or A;

$X_{n2}$ is F, V, A, K, R, G, S, I or L;

$X_{n3}$ is H, Q, E, G, D, A, or V; and $X_{n4}$ is E, G, V, A, P, D, T or M.

4. The isolated polypeptide of claim 2, wherein $X_{n1}$ is absent;

$X_{n2}$ is F, V, A, K, R, G, S, I or L;

$X_{n3}$ is H, Q, E, G, D, A, or V; and $X_{n4}$ is E, G, V, A, P, D, T or M.

5. The isolated polypeptide of claim 2, wherein $X_{n1}$ is an acidic amino acid.

6. The isolated polypeptide of claim 2, wherein $X_{n2}$ is a branched-chain amino acid or K.

7. The isolated polypeptide of claim 2, wherein $X_{n3}$ is an acidic amino acid or V.

8. The isolated polypeptide of claim 2, wherein $X_{n4}$ is V or G.

9. The isolated polypeptide of claim 1, wherein $X_1$ is a neutral and hydrophobic, neutral and polar, or basic amino acid.

10. The isolated polypeptide of claim 9, wherein $X_1$ is R, I, G, Q, L, T or S.

11. The isolated polypeptide of claim 10, wherein $X_1$ is R or I.

12. The isolated polypeptide of claim 1, wherein $X_2$ is a neutral and hydrophobic, neutral and polar, or basic amino acid.

13. The isolated polypeptide of claim 12, wherein $X_2$ is R, P, W, G, L or N.

14. The isolated polypeptide of claim 13, wherein $X_2$ is R.

15. The isolated polypeptide of claim 1, wherein $X_3$ is a neutral and polar, or basic amino acid.

16. The isolated polypeptide of claim 15, wherein $X_3$ is H, Q or N.

17. The isolated polypeptide of claim 1, wherein $X_4$ is a neutral and polar, basic, or acidic amino acid.

18. The isolated polypeptide of claim 17, wherein $X_4$ is Q, N, S, K or E.

19. The isolated polypeptide of claim 18, wherein $X_4$ is K or N.

20. The isolated polypeptide of claim 1, wherein $X_5$ is a neutral and polar, neutral and hydrophobic, or acidic amino acid.

21. The isolated polypeptide of claim 20, wherein $X_5$ is V, A, Y, D or E.

22. The isolated polypeptide of claim 21, wherein $X_5$ is D or E.

23. The isolated polypeptide of claim 1, wherein $X_c$ is $X_{c1}$-$X_{c2}$ and wherein $X_{c1}$ is a neutral and polar, or neutral and hydrophobic amino acid, and $X_{c2}$ is a neutral and polar, neutral and hydrophobic, or basic amino acid.

24. The isolated polypeptide of claim 23, wherein $X_{c1}$ is L, I, P, F, M, Q or G.

25. The isolated polypeptide of claim 24, wherein $X_{c1}$ is L or Q.

26. The isolated polypeptide of claim 23, wherein $X_{c2}$ is M, W, T, S, G, N or R.

27. The isolated polypeptide of claim 26, wherein $X_{c2}$ is G or R.

28. An isolated polypeptide having the amino acid sequence of SEQ ID NO:81.

29. An isolated polypeptide having the amino acid sequence of SEQ ID NO:82.

30. A method of activating a human erythropoietin receptor, comprising the steps of:

contacting a cell having an erythropoietin receptor on it surface with a peptide mimetic of erythropoietin, wherein said peptide mimetic is a compound having the general formula according to claim 1; and allowing said peptide mimetic to bind to said erythropoietin receptor, thereby initiating activation of said erythropoietin receptor.

31. A method of inhibiting binding of erythropoietin to an erythropoietin receptor, comprising the steps of:

providing a peptide mimetic having the general formula according to claim 1 in sufficient quantity to compete with erythropoietin for binding to an erythropoietin receptor; and allowing said peptide mimetic to interact with said erythropoietin receptor, thereby inhibiting binding of erythropoietin to said erythropoietin receptor.

32. The method of claim 31, wherein said erythropoietin receptor is derived from a human.

\* \* \* \* \*

SEQUENCE LISTING (1) GENERAL INFORMATION:

(iii) NUMBER OF SEQUENCES: 90

(2) INFORMATION FOR SEQ ID NO: 1:

(i) SEQUENCE CHARACTERISTICS:
      (A) LENGTH: 14 amino acids
      (B) TYPE: amino acid
      (C) STRANDEDNESS: single
      (D) TOPOLOGY: linear (xi) SEQUENCE DESCRIPTION: SEQ ID NO: 1:

Tyr Xaa Cys Xaa Xaa Gly Pro Xaa Thr Trp Xaa Cys Xaa Pro
1               5                   10

(2) INFORMATION FOR SEQ ID NO: 2:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (xi) SEQUENCE DESCRIPTION: SEQ ID NO: 2:

AGCTTCGAGC GGCCGCCGTG CCCAGGGATT GTGGTTGTAA G          41

(2) INFORMATION FOR SEQ ID NO: 3:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

GATCCTCGAG TCATTTACCA GGAGAGTGGG AGAGGCT          37

(2) INFORMATION FOR SEQ ID NO: 4:

(i) SEQUENCE CHARACTERISTICS:
      (A) LENGTH: 6338 base pairs
      (B) TYPE: nucleic acid
      (C) STRANDEDNESS: single
      (D) TOPOLOGY: linear (xi) SEQUENCE DESCRIPTION: SEQ ID NO: 4:

GACGGATCGG GAGATCTCCC GATCCCCTAT GGTCGACTCT CAGTACAATC TGCTCTGATG    60

CCGCATAGTT AAGCCAGTAT CTGCTCCCTG CTTGTGTGTT GGAGGTCGCT GAGTAGTGCG   120

CGAGCAAAAT TTAAGCTACA ACAAGGCAAG GCTTGACCGA CAATTGCATG AAGAATCTGC   180

TTAGGGTTAG GCGTTTTGCG CTGCTTCGCG ATGTACGGGC CAGATATACG CGTTGACATT   240

-continued

```
GATTATTGAC TAGTTATTAA TAGTAATCAA TTACGGGGTC ATTAGTTCAT AGCCCATATA    300

TGGAGTTCCG CGTTACATAA CTTACGGTAA ATGGCCCGCC TGGCTGACCG CCCAACGACC    360

CCCGCCCATT GACGTCAATA ATGACGTATG TTCCCATAGT AACGCCAATA GGGACTTTCC    420

ATTGACGTCA ATGGGTGGAC TATTTACGGT AAACTGCCCA CTTGGCAGTA CATCAAGTGT    480

ATCATATGCC AAGTACGCCC CCTATTGACG TCAATGACGG TAAATGGCCC GCCTGGCATT    540

ATGCCCAGTA CATGACCTTA TGGGACTTTC CTACTTGGCA GTACATCTAC GTATTAGTCA    600

TCGCTATTAC CATGGTGATG CGGTTTTGGC AGTACATCAA TGGGCGTGGA TAGCGGTTTG    660

ACTCACGGGG ATTTCCAAGT CTCCACCCCA TTGACGTCAA TGGGAGTTTG TTTTGGCACC    720

AAAATCAACG GGACTTTCCA AAATGTCGTA ACAACTCCGC CCCATTGACG CAAATGGGCG    780

GTAGGCGTGT ACGGTGGGAG GTCTATATAA GCAGAGCTCT CTGGCTAACT AGAGAACCCA    840

CTGCTTACTG GCTTATCGAA ATTAATACGA CTCACTATAG GGAGACCCAA GCTGGCTAGC    900

GTTTAAACTT AAGCTTGGTA CCGAGCTCGG ATCCACTAGT CCAGTGTGGT GGAATTCTGC    960

AGATATCCAG CACAGTGGCG GCCGCCGTGC CAGGGATTG TGGTTGTAAG CCTTGCATAT    1020

GTACAGGTAA GTCAGTGGCC TTCACCTGAC CCAGATGCAA CAAGTGGCAA TGGTTGGAGG    1080

GTGGCCAGGT ATTGACCTAT TTCCACCTTT CTTCTTCATC CTTAGTCCCA GAAGTATCAT    1140

CTGTCTTCAT CTTCCCCCCA AAGCCCAAGG ATGTGCTCAC CATTACTCTG ACTCCTAAGG    1200

TCACGTGTGT TGTGGTAGAC ATCAGCAAGG ATGATCCCGA GGTCCAGTTC AGCTGGTTTG    1260

TAGATGATGT GGAGGTGCAC ACAGCTCAGA CGCAACCCCG GGAGGAGCAG TTCAACAGCA    1320

CTTTCCGCTC AGTCAGTGAA CTTCCCATCA TGCACCAGGA CTGGCTCAAT GGCAAGGAGT    1380

TCAAATGCAG GGTCAACAGT GCAGCTTTCC CTGCCCCCAT CGAGAAAACC ATCTCCAAAA    1440

CCAAAGGTGA GAGCTGCAGT GTGTGACATA GAAGCTGCAA TAGTCAGTCC ATAGACAGAG    1500

CTTGGCATAA CAGACCCCTG CCCTGTTCGT GACCTCTGTG CTGACCAATC TCTTTACCCA    1560

CCCACAGGCA GACCGAAGGC TCCACAGGTG TACACCATTC CACCTCCCAA GGAGCAGATG    1620

GCCAAGGATA AAGTCAGTCT GACCGCCATG ATAACAGACT TCTTCCCTGA AGACATTACT    1680

GTGGAGTGGC AGTGGAATGG GCAGCCAGCG GAGAACTACA AGAACACTCA GCCCATCATG    1740

AACACGAATG GCTCTTACTT CGTCTACAGC AAGCTCAATG TGCAGAAGAG CAACTGGGAG    1800

GCAGGAAATA CTTTCACCTG CTCTGTGTTA CATGAGGGCC TACACAACCA CCATACTGAG    1860

AAGAGCCTCT CCCACTCTCC TGGTAAATGA CTCGAGTCTA GAGGGCCCGT TTAAACCCGC    1920

TGATCAGCCT CGACTGTGCC TTCTAGTTGC CAGCCATCTG TTGTTTGCCC CTCCCCCGTG    1980

CCTTCCTTGA CCCTGGAAGG TGCCACTCCC ACTGTCCTTT CCTAATAAAA TGAGGAAATT    2040

GCATCGCATT GTCTGAGTAG GTGTCATTCT ATTCTGGGGG GTGGGGTGGG GCAGGACAGC    2100

AAGGGGGAGG ATTGGGAAGA CAATAGCAGG CATGCTGGGG ATGCGGTGGG CTCTATGGCT    2160

TCTGAGGCGG AAAGAACCAG CTGGGGCTCT AGGGGGTATC CCCACGCGCC CTGTAGCGGC    2220

GCATTAAGCG CGGCGGGTGT GGTGGTTACG CGCAGCGTGA CCGCTACACT TGCCAGCGCC    2280

CTAGCGCCCG CTCCTTTCGC TTTCTTCCCT TCCTTTCTCG CCACGTTCGC CGGCTTTCCC    2340

CGTCAAGCTC TAAATCGGGG CATCCCTTTA GGGTTCCGAT TTAGTGCTTT ACGGCACCTC    2400

GACCCCAAAA AACTTGATTA GGGTGATGGT TCACGTAGTG GGCCATCGCC CTGATAGACG    2460

GTTTTTCGCC CTTTGACGTT GGAGTCCACG TTCTTTAATA GTGGACTCTT GTTCCAAACT    2520

GGAACAACAC TCAACCCTAT CTCGGTCTAT TCTTTTGATT TATAAGGGAT TTTGGGGATT    2580

TCGGCCTATT GGTTAAAAAA TGAGCTGATT TAACAAAAAT TAACGCGAA TTAATTCTGT    2640
```

```
GGAATGTGTG TCAGTTAGGG TGTGGAAAGT CCCCAGGCTC CCCAGGCAGG CAGAAGTATG      2700

CAAAGCATGC ATCTCAATTA GTCAGCAACC AGGTGTGGAA AGTCCCCAGG CTCCCCAGCA      2760

GGCAGAAGTA TGCAAAGCAT GCATCTCAAT TAGTCAGCAA CCATAGTCCC GCCCCTACTA      2820

CCGCCCATCC CGCCCCTAAC TCCGCCCAGT TCCGCCCATT CTCCGCCCCA TGGCTGATAG      2880

ATTTTTTTTA TTTATGCAGA GGCCGAGGCC GCCTCTGCCT CTGAGCTATT CCAGAAGTAG      2940

TGAGGAGGCT TTTTTGGAGG CCTAGGCTTT TGCAAAAAGC TCCCGGGAGC TTGTATATCC      3000

ATTTTCGGAT CTGATCAAGA GACAGGATGA GGATCGTTTC GCATGATTGA ACAAGATGGA      3060

TTGCACGCAG GTTCTCCGGC CGCTTGGGTG GAGAGGCTAT TCGGCTATGA CTGGGCACAA      3120

CAGACAATCG GCTGCTCTGA TGCCGCCGTG TTCCGGCTGT CAGCGCAGGG GCGCCCGGTT      3180

CTTTTTGTCA AGACCGACCT GTCCGGTGCC CTGAATGAAC TGCAGGACGA GGCAGCGCGG      3240

CTATCGTGGC TGGCCACGAC GGGCGTTCCT TGCGCAGCTG TGCTCGACGT TGTCACTGAA      3300

GCGGGAAGGG ACTGGCTGCT ATTGGGCGAA GTGCCGGGGC AGGATCTCCT GTCATCTCAC      3360

CTTGCTCCTG CCGAGAAAGT ATCCATCATG GCTGATGCAA TGCGGCGGCT GCATACGCTT      3420

GATCCGGCTA CCTGCCCATT CGACCACCAA GCGAAACATC GCATCGAGCG AGCACGTACT      3480

CGGATGGAAG CCGGTCTTGT CGATCAGGAT GATCTGGACG AAGAGCATCA GGGGCTCGCG      3540

CCAGCCGAAC TGTTCGCCAG GCTCAAGGCG CGCATGCCCG ACGGCGAGGA TCTCGTCGTG      3600

ACCCATGGCG ATGCCTGCTT GCCGAATATC ATGGTGGAAA ATGGCCGCTT TTCTGGATTC      3660

ATCGACTGTG GCCGGCTGGG TGTGGCGGAC CGCTATCAGG ACATAGCGTT GGCTACCCGT      3720

GATATTGCTG AAGAGCTTGG CGGCGAATGG GCTGACCGCT TCCTCGTGCT TTACGGTATC      3780

GCCGCTCCCG ATTCGCAGCG CATCGCCTTC TATCGCCTTC TTGACGAGTT CTTCTGAGCG      3840

GGACTCTGGG GTTCGAAATG ACCGACCAAG CGACGCCCAA CCTGCCATCA CGAGATTTCG      3900

ATTCCACCGC CGCCTTCTAT GAAAGGTTGG GCTTCGGAAT CGTTTTCCGG GACGCCGGCT      3960

GGATGATCCT CCAGCGCGGG GATCTCATGC TGGAGTTCTT CGCCCACCCC AACTTGTTTA      4020

TTGCAGCTTA TAATGGTTAC AAATAAAGCA ATAGCATCAC AAATTTCACA AATAAAGCAT      4080

TTTTTTCACT GCATTCTAGT TGTGGTTTGT CCAAACTCAT CAATGTATCT TATCATGTCT      4140

GTATACCGTC GACCTCTAGC TAGAGCTTGG CGTAATCATG GTCATAGCTG TTTCCTGTGT      4200

GAAATTGTTA TCCGCTCACA ATTCCACACA ACATACGAGC CGGAAGCATA AAGTGTAAAG      4260

CCTGGGGTGC CTAATGAGTG AGCTAACTCA CATTAATTGC GTTGCGCTCA CTGCCCGCTT      4320

TCCAGTCGGG AAACCTGTCG TGCCAGCTGC ATTAATGAAT CGGCCAACGC GCGGGGAGAG      4380

GCGGTTTGCG TATTGGGCGC TCTTCCGCTT CCTCGCTCAC TGACTCGCTG CGCTCGGTCG      4440

TTCGGCTGCG GCGAGCGGTA TCAGCTCACT CAAAGGCGGT AATACGGTTA TCCACAGAAT      4500

CAGGGGATAA CGCAGGAAAG AACATGTGAG CAAAAGGCCA GCAAAAGGCC AGGAACCGTA      4560

AAAAGGCCGC GTTGCTGGCG TTTTTCCATA GGCTCCGCCC CCTGACGAG CATCACAAAA      4620

ATCGACGCTC AAGTCAGAGG TGGCGAAACC CGACAGGACT ATAAAGATAC CAGGCGTTTC      4680

CCCCTGGAAG CTCCCTCGTG CGCTCTCCTG TTCCGACCCT GCCGCTTACC GGATACCTGT      4740

CCGCCTTTCT CCCTTCGGGA AGCGTGGCGC TTTCTCAATG CTCACGCTGT AGGTATCTCA      4800

GTTCGGTGTA GGTCGTTCGC TCCAAGCTGG GCTGTGTGCA CGAACCCCCC GTTCAGCCCG      4860

ACCGCTGCGC CTTATCCGGT AACTATCGTC TTGAGTCCAA CCCGGTAAGA CACGACTTAT      4920

CGCCACTGGC AGCAGCCACT GGTAACAGGA TTAGCAGAGC GAGGTATGTA GGCGGTGCTA      4980

CAGAGTTCTT GAAGTGGTGG CCTAACTACG GCTACACTAG AAGGACAGTA TTTGGTATCT      5040
```

```
GCGCTCTGCT GAAGCCAGTT ACCTTCGGAA AAAGAGTTGG TAGCTCTTGA TCCGGCAAAC      5100

AAACCACCGC TGGTAGCGGT GGTTTTTTTG TTTGCAAGCA GCAGATTACG CGCAGAAAAA      5160

AAGGATCTCA AGAAGATCCT TTGATCTTTT CTACGGGGTC TGACGCTCAG TGGAACGAAA      5220

ACTCACGTTA AGGGATTTTG GTCATGAGAT TATCAAAAAG GATCTTCACC TAGATCCTTT      5280

TAAATTAAAA ATGAAGTTTT AAATCAATCT AAAGTATATA TGAGTAAACT TGGTCTGACA      5340

GTTACCAATG CTTAATCAGT GAGGCACCTA TCTCAGCGAT CTGTCTATTT CGTTCATCCA      5400

TAGTTGCCTG ACTCCCCGTC GTGTAGATAA CTACGATACG GGAGGGCTTA CCATCTGGCC      5460

CCAGTGCTGC AATGATACCG CGAGACCCAC GCTCACCGGC TCCAGATTTA TCAGCAATAA      5520

ACCAGCCAGC CGGAAGGGCC GAGCGCAGAA GTGGTCCTGC AACTTTATCC GCCTCCATCC      5580

AGTCTATTAA TTGTTGCCGG GAAGCTAGAG TAAGTAGTTC GCCAGTTAAT AGTTTGCGCA      5640

ACGTTGTTGC CATTGCTACA GGCATCGTGG TGTCACGCTC GTCGTTTGGT ATGGCTTCAT      5700

TCAGCTCCGG TTCCCAACGA TCAAGGCGAG TTACATGATC CCCCATGTTG TGCAAAAAAG      5760

CGGTTAGCTC CTTCGGTCCT CCGATCGTTG TCAGAAGTAA GTTGGCCGCA GTGTTATCAC      5820

TCATGGTTAT GGCAGCACTG CATAATTCTC TTACTGTCAT GCCATCCGTA AGATGCTTTT      5880

CTGTGACTGG TGAGTACTCA ACCAAGTCAT TCTGAGAATA GTGTATGCGG CGACCGAGTT      5940

GCTCTTGCCC GGCGTCAATA CGGGATAATA CCGCGCCACA TAGCAGAACT TTAAAAGTGC      6000

TCATCATTGG AAAACGTTCT TCGGGGCGAA AACTCTCAAG GATCTTACCG CTGTTGAGAT      6060

CCAGTTCGAT GTAACCCACT CGTGCACCCA ACTGATCTTC AGCATCTTTT ACTTTCACCA      6120

GCGTTTCTGG GTGAGCAAAA ACAGGAAGGC AAAATGCCGC AAAAAAGGGA ATAAGGGCGA      6180

CACGGAAATG TTGAATACTC ATACTCTTCC TTTTTCAATA TTATTGAAGC ATTTATCAGG      6240

GTTATTGTCT CATGAGCGGA TACATATTTG AATGTATTTA GAAAAATAAA CAAATAGGGG      6300

TTCCGCGCAC ATTTCCCCGA AAAGTGCCAC CTGACGTC                              6338

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 5:

GATCGGATCC ATGGACCACC TCGGGGCGTC CCTC                                  34

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 6:

AGCTTCGAGC GGCCGCGGGG TCCAGGTCGC TAGGCGTCAG                            40

(2) INFORMATION FOR SEQ ID NO: 7:

(i) SEQUENCE CHARACTERISTICS:
        (A) LENGTH: 750 base pairs
        (B) TYPE: nucleic acid
        (C) STRANDEDNESS: single
        (D) TOPOLOGY: linear
```

(xi) SEQUENCE DESCRIPTION: SEQ ID NO: 7:

```
ATGGACCACC TCGGGGCGTC CCTCTGGCCC CAGGTCGGCT CCCTTTGTCT CCTGCTCGCT      60
GGGGCCGCCT GGGCGCCCCC GCCTAACCTC CCGGACCCCA AGTTCGAGAG CAAAGCGGCC     120
TTGCTGGCGG CCCGGGGGCC CGAAGAGCTT CTGTGCTTCA CCGAGCGGTT GGAGGACTTG     180
GTGTGTTTCT GGGAGGAAGC GGCGAGCGCT GGGGTGGGCC CGGGCAACTA CAGCTTCTCC     240
TACCAGCTCG AGGATGAGCC ATGGAAGCTG TGTCGCCTGC ACCAGGCTCC CACGGCTCGT     300
GGTGCGGTGC GCTTCTGGTG TTCGCTGCCT ACAGCCGACA CGTCGAGCTT CGTGCCCCTA     360
GAGTTGCGCG TCACAGCAGC CTCCGGCGCT CCGCGATATC ACCGTGTCAT CCACATCAAT     420
GAAGTAGTGC TCCTAGACGC CCCCGTGGGG CTGGTGGCGC GGTTGGCTGA CGAGAGCGAC     480
CACGTAGTGT TGCGCTGGCT CCCGCCGCCT GAGACACCCA TGACGTCTCA CATCCGCTAC     540
GAGGTGGACG TCTCGGCCGG CAACGGCGCA GGGAGCGTAC AGAGGGTGGA GATCCTGGAG     600
GGCCGCACCG AGTGTGTGCT GAGCAACCTG CGGGGCCGGA CGCGCTACAC CTTCGCCGTC     660
CGCGCGCGTA TGGCTGAGCC GAGCTTCGGC GGCTTCTGGA GCGCCTGGTC GGAGCCTGTG     720
TCGCTGCTGA CGCCTAGCGA CCTGGACCCC                                     750
```

(2) INFORMATION FOR SEQ ID NO: 8:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 8:

```
GACTTCGATG TGTGCAGGAG GGGTTGGGTG GGGCATTGCA AGGATTGGTT GAGCGACGAG      60
TACGCCAGCA ATCCTAGCTA CCCCGTCCCG CATAGTTACT ACCTCAACCC TCCC           114
```

(2) INFORMATION FOR SEQ ID NO: 9:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 9:

```
Asp Phe Asp Val Cys Arg Arg Gly Trp Val Gly His Cys Lys Asp Trp
 1               5                  10                  15
Leu Ser Asp Glu Tyr Ala Ser Asn Pro Ser Tyr Pro Val Pro His Ser
            20                  25                  30
Tyr Tyr Leu Asn Pro Pro
            35
```

(2) INFORMATION FOR SEQ ID NO: 10:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 10:

Gly Ala Ser Thr Thr Ser Gly Ala Ser Gly Thr Ser Thr Gly Ser Cys
1               5                   10                  15

Gly Ser Cys Gly Ser Gly Gly Ser Thr Gly Ser Gly Thr Ser Gly Gly
                20                  25                  30

Ser Cys Ala Ser Thr Gly Ser Ala Ala Ser Gly Ala Ser Thr Gly Ser
            35                  40                  45

Cys Thr Ser Ala Gly Ser Gly Ala Cys Gly Ala Gly Thr Ala Cys
50                  55                  60

(2) INFORMATION FOR SEQ ID NO: 11:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 11:

Ser Gly Gly Ser Gly Gly Ser Thr Thr Ser Ala Gly Ser Thr Ala Ser
1               5                   10                  15

Thr Ala Ser Cys Thr Ser Thr Gly Ser Gly Gly Ser Ala Cys Ser Gly
                20                  25                  30

Gly Ser Thr Ala Ser Cys Thr Ser Gly Gly Ser Thr Thr Ser Cys Thr
            35                  40                  45

Ser Gly Cys Gly Thr Ala Cys Thr Cys Gly Thr Cys
50                  55                  60

(2) INFORMATION FOR SEQ ID NO: 12:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 12:

Cys Xaa Xaa Gly Trp Val Gly Xaa Cys Xaa Xaa Trp
1               5                   10

(2) INFORMATION FOR SEQ ID NO: 13:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 13:

GACGTTCACG AATGCCGTCC GGGTTGGGTT GGTCACTGCA AAGACTGGCT GTCTGACGAG    60

TACGCTTCTA ACCGTCGTTC TCCGGAACCG CACCGTAACT ACCCGATCCC GCCG         114

(2) INFORMATION FOR SEQ ID NO: 14:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 14:

GAAGCTCAGG GTTGCCGTTG GGGTTGGGTT GGTAACTGCA AAGAATGGCT GGGTGACGAA    60

TACGCTAAAA ACACCGGTAC CCCGGCTGAA AAAGGTAAAT CTCGTAACCC GCCG    114

(2) INFORMATION FOR SEQ ID NO: 15:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 15:

GGTAAAGAAG TTTGCCGTCG TGGTTGGGTT GGTCACTGCC AGGAATGGCC GATGGACGAA    60

TACACCCGTA ACCCGTCTCA CCCGGTTCCG CACAACTCTC GTCACAAAAC CCCG    114

(2) INFORMATION FOR SEQ ID NO: 16:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 16:

AACATCCAGG GTTGCATCCG TGGTTGGGTT GGTCAGTGCA AAGACTGGCT GCGTGACGAA    60

TACGCTCGTG AACACACCAA CCAGGAAACC CCGAACAACC TGCTGAACCC GCCG    114

(2) INFORMATION FOR SEQ ID NO: 17:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 17:

GGTCTGGGTG CTTGCCGTCG TGGTTGGGTT GGTCACTGCA ACGACTGGCT GAACGACGAA    60

TACGCTAAAA AACCGGGTTA CGCTATGCCG GACGGTTACC CGCACAACGG TACC    114

(2) INFORMATION FOR SEQ ID NO: 18:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 18:

TCTCTGGAAC CGTGCCGTGG TGGTTGGGTT GGTCACTGCA ACGAATGGCA GCGTGACGAA    60

TACGCTATCA ACCCGAAATG GCCGAACGCT CCGATCGAAG ACCCGAACCC GCTG    114

(2) INFORMATION FOR SEQ ID NO: 19:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 19:

GACCGTGAAG GTTGCCGTCG TGGTTGGGTT GGTCAGTGCA AAGCTTGGTT CAACGACGAA     60

TACGCTAAAC CGCCGAAAAA ACCGTTCCGT AACTCTTACT CTCTGGGTCC GGCT          114

(2) INFORMATION FOR SEQ ID NO: 20:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 20:

GACTTCGAAG ACTGCCAGGG TGGTTGGGTT GGTCACTGCA ACGACTGGCT GGGTGACGAA     60

TACGCTCGTC ACCCGCGTTA CGGTGCTACC CAGACCCTGT CTGTTAACCG TCAC          114

(2) INFORMATION FOR SEQ ID NO: 21:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 21:

GACTTCGAAG ACTGCCAGGG TGGTTGGGTT GGTCACTGCA ACGACTGGCT GGGTGACGAA     60

TACGCTCGTC ACCCGCGTTA CGGTGCTACC CAGACCCTGT CTGTTAACCG TCAC          114

(2) INFORMATION FOR SEQ ID NO: 22:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 22:

GACCTGGAAG TTTGCCGTGG TGGTTGGGTT GGTCACTGCA AAGACTGGAT CTGGGACGAA     60

TACGCTCGTA ACCCGCGTTA CCCGGACCCG CAGCGTAAAG AAGTTAAATC TCCG          114

(2) INFORMATION FOR SEQ ID NO: 23:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 23:

AACATCCAGG GTTGCATCCG TGGTTGGGTT GGTCAGTGCA AAGACTGGCT GCGTGACGAA     60

TACGCTCGTG AACACACCAA CCAGGAAACC CCGAACAACC TGCTGAACCC GCCG          114

(2) INFORMATION FOR SEQ ID NO: 24:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 24:

GGTCTGGGTG CTTGCCGTCG TGGTTGGGTT GGTCACTGCA ACGACTGGCT GAACGACGAA    60

TACGCTAAAA AACCGGGTTA CGCTATGCCG GACGGTTACC CGCACAACGG TACC    114

(2) INFORMATION FOR SEQ ID NO: 25:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 25:

GAAGGTGAAG TTTGCCTGCC GGGTTGGGTT GGTCACTGCA AATACTGGCT GATGGACGAA    60

TACGCTAACA TCCCGCGTAA CCCGACCCCG CGTTCTAACG AACTGAAACC GCCG    114

(2) INFORMATION FOR SEQ ID NO: 26:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 26:

GAAGCTCAGG GTTGCCGTTG GGGTTGGGTT GGTAACTGCA AAGAATGGCT GGGTGACGAA    60

TACGCTAAAA ACACCGGTAC CCCGGCTGAA AAAGGTAAAT CTCGTAACCC GCCG    114

(2) INFORMATION FOR SEQ ID NO: 27:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 27:

CAGGTTGACA CCTGCACCCG TGGTTGGGTT GGTCACTGCA ACGCTTGGAT GGGTGACGAA    60

TACGCTAAAA CCCCGGGTCT GCCGATGCCG CAGTCTGACT ACCTGAAACC GCGT    114

(2) INFORMATION FOR SEQ ID NO: 28:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 28:

GACGTTGAAG TTTGCCGTGG TGGTTGGGTT GGTCACTGCA ACGCTTGGCT GCGTGACGAA    60

TACAACCGTC AGCCGAAAAA ACCGGTTCAG CAGCAGGTTG TTTACTCTAC CCGT    114

(2) INFORMATION FOR SEQ ID NO: 29:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 29:

CTGCTGCAGA TGTGCTCTCC GGGTTGGGTT GGTCACTGCA ACGACTGGCC GCGTGACGAA    60

TACGCTAACA ACCCGCCGAA CCCGGTTGTT GACCGTCAGG CTCTGACCCC GCCG          114

(2) INFORMATION FOR SEQ ID NO: 30:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 30:

TACTCTGACG TTTGCCGTCG TGGTTGGGTT GGTCACTGCG AAGACTGGCT GGGTGACGAA    60

TACTCTTCTC AGCCGTCTTA CGCTCTGCCG CACTCTACCT CTCTGAACCC GCGT          114

(2) INFORMATION FOR SEQ ID NO: 31:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 31:

GACCTGGAAG GTTGCCGTCT GGGTTGGGTT GGTCACTGCA ACGTTTGGGG TGGTGACGAA    60

TACACCAAAC GTACCTCTCA CTCTGTTCCG CCGTCTCACA AATCTAAACT GCTG          114

(2) INFORMATION FOR SEQ ID NO: 32:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 32:

GACCTGGCTG GTTGCCGTCG TGGTTGGGTT GGTCACTGCT CTGAATGGCT GCGTGACGAA    60

TACACCTCTA ACCCGCGTTA CCCGGTTGCT CCGTCTTACC GTCTGCAGCC GCCG          114

(2) INFORMATION FOR SEQ ID NO: 33:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 33:

GCTAAAGTTG TTTGCCGTAA CGGTTGGGTT GGTCACTGCT CTGCTTGGCT GACCGACGAA    60

TACGAATCTA ACCCGAACAC CCGTATCCCG AACACCTTCG ACATGAAAAC CCCG          114

(2) INFORMATION FOR SEQ ID NO: 34:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 34:

CGTCTGGAAG ACGGTGACGA AGGTCGTGTT TGGCACTCTT CTGACCTGCT GTCTGACGAA      60

TACGCTTCTA CCCCGTCTTA CCCGCTGACC CCGAACTACT ACGAATACCC GCCG           114

(2) INFORMATION FOR SEQ ID NO: 35:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 35:

GGTTGGGCTG GTTGCCGTTC TGGTGGTGCT GGTCAGTGCA AGAAGGTGC TGGTGACGAA       60

TACGCTGAAA ACCCGTCTTA CCCGGTTCCG CCGCGTAAAC ACCTGAACCG TCTG           114

(2) INFORMATION FOR SEQ ID NO: 36:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 36:

GACCTGAACG TTGGTTGCCC GGGTTACGTT GGTCACTGCG CTGACTGGCT GGGTGACGAA      60

TACCCGGTTC ACCCGAACCC GGAAGTTCCG CAGACCCTGA ACCTGAAACC GCAC           114

(2) INFORMATION FOR SEQ ID NO: 37:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 37:

GAACTGGACA TGCTGCGTGG TGGTGGTGTT GGTCAGTCTA AAGAATCTCT GCGTGACGAA      60

TACGACCACA AAACCTCTAC CCCGGTTCCG CCGAACCAGA AACTGCCGCC GCCG           114

(2) INFORMATION FOR SEQ ID NO: 38:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 38:

AACTCTGACG TTACCCGTCG TGGTTGGGCT GACCACTGGC GTGAATGGAA CTGGGACGAA      60

TACGCTTCTA CCCCGACCCA CCCGGCTTCT CACTCTTCTT ACCTGAACCC GCCG           114

(2) INFORMATION FOR SEQ ID NO: 39:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 39:

GAATGGGTTT ACTCTCGTCA GTCTTGGGGT GGTCAGTGGA AAGACGGTGT TCGTGACGAA      60

TACACCATGA CCCCGGGTGA CCCGGTTGCT AACAAATACT CTCTGATGAC CCCG      114

(2) INFORMATION FOR SEQ ID NO: 40:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 40:

GAATTCGTTG TTTGGCCGCG TGGTTGGGTT GGTCACTGCA AAGGTTGCCG TGTTGACGAA      60

TACTCTGGTG ACCCGTCTAA CCTGGAAGCT CAGACCCACG ACATGAACTT CCAG      114

(2) INFORMATION FOR SEQ ID NO: 41:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 41:

GGTCTGAACA TCTGCCGTCC GGGTTGGGTT GGTCACTGCA ACGACTCTCT GCGTGACGAA      60

TACGCTACCA ACCCGCGTAC CCCGGGTCCG CTGTCTTACA ACCTGCAGCC GACC      114

(2) INFORMATION FOR SEQ ID NO: 42:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 42:

TCTGTTGACG TTTGCAACCA GGGTGGTGTT GGTCGTTGCA ACGACGGTCT GGGTGACGAA      60

TACGCTTCTA AACCGTCTTA CCAGGAAGCT CCGCGTTACA ACCCGAACCT GCGT      114

(2) INFORMATION FOR SEQ ID NO: 43:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 43:

GACTTCGAAG GTTCTCTGCG TGAATGGGAC GGTGACTGGC CGGAATGGCT GCGTGACGAA      60

TACGCTCGTC AGCCGTCTTA CCCGAACCCG CACAAAGCTA ACCAGAAACC GCCG      114

(2) INFORMATION FOR SEQ ID NO: 44:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 44:

GCTCTGGACG TTGGTCGTTG GGACGGTGTT GGTCACTGCA AAGGTTGCCT GAAAGACGAA        60

TACACCACCC TGGACTCTAA AAACGTTCCG CAGATCTCTC AGGTTTCTCC GACC             114

(2) INFORMATION FOR SEQ ID NO: 45:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO: 45:

GACGTTGAAG TTGGTCGTCG TGCTTGCGTT GGTTACTGCC AGGAATTCCT GCGTGACGAA        60

TACACCGCTA CCCCGTCTTA CCCGGACAAA CACTCTAACT ACCTGAACCC GCCG             114

(2) INFORMATION FOR SEQ ID NO: 46:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

GACATCGCTG TTTGCCGTGG TGGTTGCGTT GGTCTGTGCG AAGAAGGTCT GCGTGACGAA        60

TACGCTTGCA ACGTTAAAAA ACCGGTTCCG CACTCTTACA AACTGAACAC CCCG             114

(2) INFORMATION FOR SEQ ID NO: 47:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 47:

Asp Val His Glu Cys Arg Pro Gly Trp Val Gly His Cys Lys Asp Trp
1               5                   10                  15

Leu Ser Asp Glu Tyr Ala Ser Asn Arg Arg Ser Pro Glu Pro His Arg
                20                  25                  30

Asn Tyr Pro Ile Pro Pro
            35

(2) INFORMATION FOR SEQ ID NO: 48:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 48:

Glu Ala Gln Gly Cys Arg Trp Gly Trp Val Gly Asn Cys Lys Glu Trp
1               5                   10                  15

```
Leu Gly Asp Glu Tyr Ala Lys Asn Thr Gly Thr Pro Ala Glu Lys Gly
            20                  25                  30

Lys Ser Arg Asn Pro Pro
        35
```

(2) INFORMATION FOR SEQ ID NO: 49:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 49:

```
Gly Lys Glu Val Cys Arg Arg Gly Trp Val Gly His Cys Gln Glu Trp
1               5                   10                  15

Pro Met Asp Glu Tyr Thr Arg Asn Pro Ser His Pro Val Pro His Asn
            20                  25                  30

Ser Arg His Lys Thr Pro
        35
```

(2) INFORMATION FOR SEQ ID NO: 50:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 50:

```
Asn Ile Gln Gly Cys Ile Arg Gly Trp Val Gly Gln Cys Lys Asp Trp
1               5                   10                  15

Leu Arg Asp Glu Tyr Ala Arg Glu His Thr Asn Gln Glu Thr Pro Asn
            20                  25                  30

Asn Leu Leu Asn Pro Pro
        35
```

(2) INFORMATION FOR SEQ ID NO: 51:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 51:

```
Gly Leu Gly Ala Cys Arg Arg Gly Trp Val Gly His Cys Asn Asp Trp
1               5                   10                  15

Leu Asn Asp Glu Tyr Ala Lys Lys Pro Gly Tyr Ala Met Pro Asp Gly
            20                  25                  30

Tyr Pro His Asn Gly Thr
        35
```

(2) INFORMATION FOR SEQ ID NO: 52:

(i) SEQUENCE CHARACTERISTICS:
        (A) LENGTH: 38 amino acids
        (B) TYPE: amino acid (C) STRANDEDNESS: single
        (D) TOPOLOGY: linear (ii) MOLECULE TYPE: None (xi) SEQUENCE DESCRIPTION: SEQ ID NO: 52:

Ser Leu Glu Pro Cys Arg Gly Gly Trp Val Gly His Cys Asn Glu Trp
1               5                   10                  15

Gln Arg Asp Glu Tyr Ala Ile Asn Pro Lys Trp Pro Asn Ala Pro Ile
            20                  25                  30

Glu Asp Pro Asn Pro Leu
        35

(2) INFORMATION FOR SEQ ID NO: 53:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 53:

Asp Arg Glu Gly Cys Arg Arg Gly Trp Val Gly Gln Cys Lys Ala Trp
1               5                   10                  15

Phe Asn Asp Glu Tyr Ala Lys Pro Pro Lys Lys Pro Phe Arg Asn Ser
            20                  25                  30

Tyr Ser Leu Gly Pro Ala
        35

(2) INFORMATION FOR SEQ ID NO: 54:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 54:

Asp Val Glu Ala Cys Gly Gly Gly Trp Val Gly His Cys Asn Tyr Trp
1               5                   10                  15

Leu Arg Asp Glu Tyr Ala Ser Lys Pro Ile Lys Gln Val Pro Pro Gly
            20                  25                  30

Asn His Asn Gln Pro Ser
        35

(2) INFORMATION FOR SEQ ID NO: 55:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 55:

Asp Phe Glu Asp Cys Gln Gly Gly Trp Val Gly His Cys Asn Asp Trp
1               5                   10                  15

```
Leu Gly Asp Glu Tyr Ala Arg His Pro Arg Tyr Gly Ala Thr Gln Thr
        20                  25                  30

Leu Ser Val Asn Arg His
        35

(2) INFORMATION FOR SEQ ID NO: 56:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 56:

Asp Leu Glu Val Cys Arg Gly Gly Trp Val Gly His Cys Lys Asp Trp
1               5                  10                  15

Ile Trp Asp Glu Tyr Ala Arg Asn Pro Arg Tyr Pro Asp Pro Gln Arg
        20                  25                  30

Lys Glu Val Lys Ser Pro
        35

(2) INFORMATION FOR SEQ ID NO: 57:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 57:

Asn Ile Gln Gly Cys Ile Arg Gly Trp Val Gly Gln Cys Lys Asp Trp
1               5                  10                  15

Leu Arg Asp Glu Tyr Ala Arg Glu His Thr Asn Gln Glu Thr Pro Asn
        20                  25                  30

Asn Leu Leu Asn Pro Pro
        35

(2) INFORMATION FOR SEQ ID NO: 58:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 58:

Gly Leu Gly Ala Cys Arg Arg Gly Trp Val Gly His Cys Asn Asp Trp
1               5                  10                  15

Leu Asn Asp Glu Tyr Ala Lys Lys Pro Gly Tyr Ala Met Pro Asp Gly
        20                  25                  30

Tyr Pro His Asn Gly Thr
        35

(2) INFORMATION FOR SEQ ID NO: 59:

(i) SEQUENCE CHARACTERISTICS:
        (A) LENGTH: 38 amino acids
        (B) TYPE: amino acid
```

(C) STRANDEDNESS: single
(D) TOPOLOGY: linear (ii) MOLECULE TYPE: None (xi) SEQUENCE DESCRIPTION: SEQ ID NO: 59:

Glu Gly Glu Val Cys Leu Pro Gly Trp Val Gly His Cys Lys Tyr Trp
1               5                   10                  15

Leu Met Asp Glu Tyr Ala Asn Ile Pro Arg Asn Pro Thr Pro Arg Ser
            20                  25                  30

Asn Glu Leu Lys Pro Pro
        35

(2) INFORMATION FOR SEQ ID NO: 60:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 60:

Glu Ala Gln Gly Cys Arg Trp Gly Trp Val Gly Asn Cys Lys Glu Trp
1               5                   10                  15

Leu Gly Asp Glu Tyr Ala Lys Asn Thr Gly Thr Pro Ala Glu Lys Gly
            20                  25                  30

Lys Ser Arg Asn Pro Pro
        35

(2) INFORMATION FOR SEQ ID NO: 61:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 61:

Gln Val Asp Thr Cys Thr Arg Gly Trp Val Gly His Cys Asn Ala Trp
1               5                   10                  15

Met Gly Asp Glu Tyr Ala Lys Thr Pro Gly Leu Pro Met Pro Gln Ser
            20                  25                  30

Asp Tyr Leu Lys Pro Arg
        35

(2) INFORMATION FOR SEQ ID NO: 62:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 62:

Asp Val Glu Val Cys Arg Gly Gly Trp Val Gly His Cys Asn Ala Trp
1               5                   10                  15

```
Leu Arg Asp Glu Tyr Asn Arg Gln Pro Lys Lys Pro Val Gln Gln Gln
            20                  25                  30

Val Val Tyr Ser Thr Arg
            35
```

(2) INFORMATION FOR SEQ ID NO: 63:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 63:

```
Leu Leu Gln Met Cys Ser Pro Gly Trp Val Gly His Cys Asn Asp Trp
1               5                   10                  15

Pro Arg Asp Glu Tyr Ala Asn Asn Pro Pro Asn Pro Val Val Asp Arg
            20                  25                  30

Gln Ala Leu Thr Pro Pro
            35
```

(2) INFORMATION FOR SEQ ID NO: 64:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 64:

```
Tyr Ser Asp Val Cys Arg Arg Gly Trp Val Gly His Cys Glu Asp Trp
1               5                   10                  15

Leu Gly Asp Glu Tyr Ser Ser Gln Pro Ser Tyr Ala Leu Pro His Ser
            20                  25                  30

Thr Ser Leu Asn Pro Arg
            35
```

(2) INFORMATION FOR SEQ ID NO: 65:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 65:

```
Asp Leu Glu Gly Cys Arg Leu Gly Trp Val Gly His Cys Asn Val Trp
1               5                   10                  15

Gly Gly Asp Glu Tyr Thr Lys Arg Thr Ser His Ser Val Pro Pro Ser
            20                  25                  30

His Lys Ser Lys Leu Leu
            35
```

(2) INFORMATION FOR SEQ ID NO: 66:

(i) SEQUENCE CHARACTERISTICS:
        (A) LENGTH: 38 amino acids
        (B) TYPE: amino acid (C) STRANDEDNESS: single
        (D) TOPOLOGY: linear (ii) MOLECULE TYPE: None (xi) SEQUENCE DESCRIPTION: SEQ ID NO: 66:

Asp Leu Ala Gly Cys Arg Arg Gly Trp Val Gly His Cys Ser Glu Trp
1               5                   10                  15

Leu Arg Asp Glu Tyr Thr Ser Asn Pro Arg Tyr Pro Val Ala Pro Ser
                20                  25                  30

Tyr Arg Leu Gln Pro Pro
            35

(2) INFORMATION FOR SEQ ID NO: 67:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 67:

Ala Lys Val Val Cys Arg Asn Gly Trp Val Gly His Cys Ser Ala Trp
1               5                   10                  15

Leu Thr Asp Glu Tyr Glu Ser Asn Pro Asn Thr Arg Ile Pro Asn Thr
                20                  25                  30

Phe Asp Met Lys Thr Pro
            35

(2) INFORMATION FOR SEQ ID NO: 68:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 68:

Arg Leu Glu Asp Gly Asp Glu Gly Arg Val Trp His Ser Ser Asp Leu
1               5                   10                  15

Leu Ser Asp Glu Tyr Ala Ser Thr Pro Ser Tyr Pro Leu Thr Pro Asn
                20                  25                  30

Tyr Tyr Glu Tyr Pro Pro
            35

(2) INFORMATION FOR SEQ ID NO: 69:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 69:

Gly Trp Ala Gly Cys Arg Ser Gly Gly Ala Gly Gln Cys Lys Glu Gly
1               5                   10                  15

-continued

```
Ala Gly Asp Glu Tyr Ala Glu Asn Pro Ser Tyr Pro Val Pro Pro Arg
            20                  25                  30
Lys His Leu Asn Arg Leu
        35
```

(2) INFORMATION FOR SEQ ID NO: 70:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 70:

```
Asp Leu Asn Val Gly Cys Pro Gly Tyr Val Gly His Cys Ala Asp Trp
1               5                   10                  15
Leu Gly Asp Glu Tyr Pro Val His Pro Asn Pro Glu Val Pro Gln Thr
            20                  25                  30
Leu Asn Leu Lys Pro His
        35
```

(2) INFORMATION FOR SEQ ID NO: 71:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 71:

```
Glu Leu Asp Met Leu Arg Gly Gly Val Gly Gln Ser Lys Glu Ser
1               5                   10                  15
Leu Arg Asp Glu Tyr Asp His Lys Thr Ser Thr Pro Val Pro Pro Asn
            20                  25                  30
Gln Lys Leu Pro Pro Pro
        35
```

(2) INFORMATION FOR SEQ ID NO: 72:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 72:

```
Asn Ser Asp Val Thr Arg Arg Gly Trp Ala Asp His Trp Arg Glu Trp
1               5                   10                  15
Asn Trp Asp Glu Tyr Ala Ser Thr Pro Thr His Pro Ala Ser His Ser
            20                  25                  30
Ser Tyr Leu Asn Pro Pro
        35
```

(2) INFORMATION FOR SEQ ID NO: 73:

(i) SEQUENCE CHARACTERISTICS:
        (A) LENGTH: 38 amino acids
        (B) TYPE: amino acid (C) STRANDEDNESS: single
            (D) TOPOLOGY: linear (ii) MOLECULE TYPE: None (xi) SEQUENCE DESCRIPTION: SEQ ID NO: 73:

Glu Trp Val Tyr Ser Arg Gln Ser Trp Gly Gly Gln Trp Lys Asp Gly
1               5                   10                  15

Val Arg Asp Glu Tyr Thr Met Thr Pro Gly Asp Pro Val Ala Asn Lys
            20                  25                  30

Tyr Ser Leu Met Thr Pro
        35

(2) INFORMATION FOR SEQ ID NO: 74:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 74:

Glu Phe Val Val Trp Pro Arg Gly Trp Val Gly His Cys Lys Gly Cys
1               5                   10                  15

Arg Val Asp Glu Tyr Ser Gly Asp Pro Ser Asn Leu Glu Ala Gln Thr
            20                  25                  30

His Asp Met Asn Phe Gln
        35

(2) INFORMATION FOR SEQ ID NO: 75:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 75:

Gly Leu Asn Ile Cys Arg Pro Gly Trp Val Gly His Cys Asn Asp Ser
1               5                   10                  15

Leu Arg Asp Glu Tyr Ala Thr Asn Pro Arg Thr Pro Gly Pro Leu Ser
            20                  25                  30

Tyr Asn Leu Gln Pro Thr
        35

(2) INFORMATION FOR SEQ ID NO: 76:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 76:

Ser Val Asp Val Cys Asn Gln Gly Gly Val Gly Arg Cys Asn Asp Gly
1               5                   10                  15

```
Leu Gly Asp Glu Tyr Ala Ser Lys Pro Ser Tyr Gln Glu Ala Pro Arg
            20                  25                  30

Tyr Asn Pro Asn Leu Arg
        35
```

(2) INFORMATION FOR SEQ ID NO: 77:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 77:

```
Asp Phe Glu Gly Ser Leu Arg Glu Trp Asp Gly Asp Trp Pro Glu Trp
1               5                   10                  15

Leu Arg Asp Glu Tyr Ala Arg Pro Ser Tyr Pro Asn Pro His Lys Ala
            20                  25                  30

Asn Gln Lys Pro Pro
        35
```

(2) INFORMATION FOR SEQ ID NO: 78:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 78:

```
Ala Leu Asp Val Gly Arg Trp Asp Gly Val Gly His Cys Lys Gly Cys
1               5                   10                  15

Leu Lys Asp Glu Tyr Thr Thr Leu Asp Ser Lys Asn Asn Pro Gln Ile
            20                  25                  30

Ser Gln Val Ser Pro Thr
        35
```

(2) INFORMATION FOR SEQ ID NO: 79:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 79:

```
Asp Val Glu Val Gly Arg Arg Ala Cys Val Gly Tyr Cys Gln Glu Phe
1               5                   10                  15

Leu Arg Asp Glu Tyr Thr Ala Thr Pro Ser Tyr Pro Asp Lys His Ser
            20                  25                  30

Asn Tyr Leu Asn Pro Pro
        35
```

(2) INFORMATION FOR SEQ ID NO: 80:

(i) SEQUENCE CHARACTERISTICS:
        (A) LENGTH: 38 amino acids
        (B) TYPE: amino acid (C) STRANDEDNESS: single
            (D) TOPOLOGY: linear (ii) MOLECULE TYPE: None (xi) SEQUENCE DESCRIPTION: SEQ ID NO: 80:

Asp Ile Ala Val Cys Arg Gly Gly Cys Val Gly Leu Cys Glu Glu Gly
1               5                   10                  15

Leu Arg Asp Glu Tyr Ala Cys Asn Val Lys Lys Pro Val Pro His Ser
            20                  25                  30

Tyr Lys Leu Asn Thr Pro
        35

(2) INFORMATION FOR SEQ ID NO: 81:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 81:

Asp Arg Glu Gly Cys Arg Arg Gly Trp Val Gly Gln Cys Lys Ala Trp
1               5                   10                  15

Phe Asn (2) INFORMATION FOR SEQ ID NO: 82:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 82:

Asp Val Glu Ala Cys Gly Gly Gly Trp Val Gly His Cys Asn Tyr Trp
1               5                   10                  15

Leu Arg (2) INFORMATION FOR SEQ ID NO: 83:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 83:

Arg Glu Gly Cys Arg Arg Gly Trp Val Gly Gln Cys Lys Ala Trp Phe
1               5                   10                  15

Asn (2) INFORMATION FOR SEQ ID NO: 84:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 84:

Glu Gly Cys Arg Arg Gly Trp Val Gly Gln Cys Lys Ala Trp Phe Asn
1               5                   10                  15

(2) INFORMATION FOR SEQ ID NO: 85:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 85:

Gly Cys Arg Arg Gly Trp Val Gly Gln Cys Lys Ala Trp Phe Asn
1               5                   10                  15

(2) INFORMATION FOR SEQ ID NO: 86:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 86:

Cys Arg Arg Gly Trp Val Gly Gln Cys Lys Ala Trp Phe Asn
1               5                   10

(2) INFORMATION FOR SEQ ID NO: 87:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 87:

Gly Gly Ala Phe Cys Glu Ala Val Gly Cys Gly Pro Asp Arg Asn Phe
1               5                   10                  15

Tyr Gly Gly (2) INFORMATION FOR SEQ ID NO: 88:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 88:

Xaa Xaa Cys Xaa Xaa Gly Trp Val Gly Xaa Cys Xaa Xaa Trp Xaa Xaa
1               5                   10                  15

(2) INFORMATION FOR SEQ ID NO: 89:

(i) SEQUENCE CHARACTERISTICS:
        (A) LENGTH: 17 amino acids
        (B) TYPE: amino acid -continued

```
            (C) STRANDEDNESS: single
            (D) TOPOLOGY: linear (ii) MOLECULE TYPE: None (xi) SEQUENCE DESCRIPTION: SEQ ID NO: 89:

Xaa Xaa Xaa Cys Xaa Xaa Gly Trp Val Gly Xaa Cys Xaa Xaa Trp Xaa Xa
1               5                   10                  15

(2) INFORMATION FOR SEQ ID NO: 90:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 90:

Xaa Xaa Xaa Xaa Cys Xaa Xaa Gly Trp Val Gly Xaa Cys Xaa Xaa Trp Xa
1               5                   10                  15

Xaa
```